(12) United States Patent
Faustman

(10) Patent No.: US 6,660,487 B2
(45) Date of Patent: Dec. 9, 2003

(54) TREATMENT OF AUTOIMMUNE DISEASE

(75) Inventor: Denise Faustman, Weston, MA (US)

(73) Assignee: The General Hospital Corporation, Boston, MA (US)

(*) Notice: Subject to any disclaimer, the term of this patent is extended or adjusted under 35 U.S.C. 154(b) by 0 days.

(21) Appl. No.: 09/768,769

(22) Filed: Jan. 23, 2001

(65) Prior Publication Data

US 2002/0123472 A1 Sep. 5, 2002

Related U.S. Application Data

(63) Continuation-in-part of application No. 09/521,064, filed on Mar. 8, 2000.
(60) Provisional application No. 60/123,738, filed on Mar. 10, 1999.

(51) Int. Cl.[7] .................. G01N 33/567; C12Q 1/06; C12N 5/00; C12N 5/06
(52) U.S. Cl. .................. 435/7.2; 435/39; 435/325; 435/334
(58) Field of Search ............. 435/7.9, 39, 325, 435/334

(56) References Cited

U.S. PATENT DOCUMENTS

| | | | |
|---|---|---|---|
| 4,309,418 A | 1/1982 | Green | 424/177 |
| 4,457,916 A | 7/1984 | Hayashi et al. | 424/101 |
| 4,495,282 A | 1/1985 | Ohnishi et al. | 435/68 |
| 4,677,063 A | 6/1987 | Mark et al. | 435/68 |
| 4,677,064 A | 6/1987 | Mark et al. | 435/68 |
| 4,681,760 A | 7/1987 | Fathman | 424/85 |
| 4,791,101 A | 12/1988 | Adolf | 514/2 |
| 4,879,226 A | 11/1989 | Wallace et al. | 435/68 |
| 4,963,354 A | 10/1990 | Shepard et al. | 424/85.1 |
| 4,985,241 A | 1/1991 | Zimmerman et al. | 424/85.1 |
| 5,002,876 A | 3/1991 | Sreekrishna et al. | 435/69.5 |
| 5,059,530 A | 10/1991 | Oshima et al. | 435/69.5 |
| 5,139,481 A | 8/1992 | Faustman et al. | 604/49 |
| 5,215,743 A | 6/1993 | Singh et al. | 424/85.1 |
| 5,283,058 A | 2/1994 | Faustman | 424/88 |
| 5,288,852 A | 2/1994 | Yamada et al. | 530/351 |
| 5,487,984 A | 1/1996 | Allet et al. | 435/69.5 |
| 5,538,854 A | 7/1996 | Faustman | 435/7.24 |
| 5,593,698 A | 1/1997 | Weiner et al. | 424/534 |
| 5,843,425 A | 12/1998 | Sachs et al. | 424/93.1 |
| 5,843,452 A | 12/1998 | Wiedmann et al. | 424/195.1 |

OTHER PUBLICATIONS

Aldrich et al., "Positive Selection of Self–and Alloreactive CD8[+] T Cells in Tap–1 Mutant Mice," *Proc. Natl. Acad. Sci. USA* 91:6525–6528 (1994).

Allen et al., "Effect of Bacillus Calmette–Guerin Vaccination on New–Onset Type 1 Diabetes," *Diabetes Care* 22:1703–1707 (1999).

Anderson et al., "Studies on the Cytophilic Properties of Human $\beta_2$ Microglobulin," *J. Immunol.* 114:997–1000 (1975).

Ashton–Rickardt et al., "Peptide Contributes to the Specificity of Positive Selection of CD8[+] T Cells in the Thymus," *Cell* 73:1041–1049 (1993).

Baldwin, "The NF–κB and IκB Proteins: New Discoveries and Insights," *Ann. Rev. Immunol.* 14:649–683 (1996).

Baeuerle and Baltimore, "NF–$_κ$B: Ten Years After," *Cell* 87:13–20 (1996).

Bernabeu et al., "$\beta_2$ –Microglobulin from Serum Associates with MHC Class I Antigens on the Surface of Cultured Cells," *Nature* 308:642–645 (1984).

(List continued on next page.)

Primary Examiner—Hankyel T. Park
(74) Attorney, Agent, or Firm—Clark & Elbing LLP

(57) ABSTRACT

The present invention features a novel combination therapy useful in the treatment of autoimmune disease that increases or maintains the number of functional cells of a predetermined type in a mammal by killing or inactivating autoimmune cells and re-educating the host immune system.

15 Claims, 8 Drawing Sheets

OTHER PUBLICATIONS

Brayer et al., "Alleles from Chromosomes 1 and 3 of NOD Mice Combine to Influence Sjögren's Syndrome–Like Autoimmune Exocrinopathy," *The Journal of Rheumatology* 27:1896–1904 (2000).

Brod et al., "New Clinical Trial in Newly Diagnosed Type 1 Diabetes," Diabetes Station Website Print–Out (2001); date visited Jun. 19, 2001 (http://www.diabetesstation.org/articles/brod.htm).

Brod et al., "Ingested Interferon α Suppresses Type 1 Diabetes in Non–Diabetic Mice," *Diabetologia* 41:1227–1232 (1998).

Faustman et al., "Linkage of Faulty Major Histocompatibility Complex Class I to Autoimmune Diabetes," *Science* 254:1756–1761 (1991).

Fu et al., "Antigen Processing and Autoimmunity: Evaluation of mRNA Abundance and Function of HLA–Linked Genes," *Annals New York Academy of Sciences* 842:138–155 (1998).

Fu et al., "Defective Major Histocompatibility Complex Class I Expression on Lymphoid Cells in Autoimmunity," *J. Clin. Invest.* 91:2301–2307 (1993).

Glas et al., "The CD8+ T Cell Repertoire in $\beta_2$–Microglobulin–Deficient Mice is Biased towards Reactivity Against Self–Major Histocompatibility Class I," *J. Exp. Med.* 179:661–672 (1994).

Graves et al., "Lack of Association between Early Childhood Immunizations and β–Cell Autoimmunity," *Diabetes Care* 22:1694–1697 (1999).

Hayashi and Faustman, "NOD Mice Are Defective in Proteasome Production and Activation of NF–κB," *Molec. and Cell. Biol.* 19:8646–8659 (1999).

Hyafil and Strominger, "Dissociation and Exchange of the $\beta_2$–Micoglobulin Subunit of HLA–A and HLA–B Antigens," *Proc. Natl. Acad. Sci. USA* 76:5834–5838 (1979).

Li and Faustman, "Use of Donor $\beta_2$–Microglobulin–Deficient Transgenic Mouse Liver Cells for Isografts, Allografts, and Xenografts," *Transplantation* 55:940–946 (1993).

Li et al., "Abnormal Class I Assembly and Peptide Presentation in the Nonobese Diabetic Mouse," *Proc. Natl. Acad. Sci. USA* 91:11128–11132 (1994).

Markiewicz et al., "Long–Term T Cell Memory Requires the Surface Expression of Self–Peptide/Major Histocompatibility Complex Molecules," *Proc. Natl. Sci. USA* 95:3065–3070 (1998).

Rabinovitch et al., "Tumor Necrosis Factor Mediates the Protective Effect of Freund's Adjuvant against Autoimmune Diabetes in BB Rats," *J. Autoimmunity* 8:357–366 (1995).

Rabinovitch et al., "TNF–α Down–Regulates Type 1 Cytokines and Prolongs Survival of Syngeneic Islet Grafts in Nonobese Diabetic Mice," *The Am. Assoc. of Immunol.* 159(12):6298–6303 (1997).

Schmidt et al., "Interspecies Exchange of $\beta_2$–Microglobulin and Associated MHC and Differentiation Antigens," *Immunogenetics* 13:483–491 (1981).

Shehadeh et al., "Effect of Adjuvant Therapy on Development of Diabetes in Mouse and Man," *Lancet* 343: 706–707 (1994).

Song et al., "Tumor Necrosis Factor–Related Apoptosis–Inducing Ligand (TRAIL) Is an Inhibitor of Autoimmune Inflammation and Cell Cycle Progression," *J. Exp. Med.,* 191:1095–1103 (2000).

Vidal–Puig and Faustman, "Tolerance to Peripheral Tissue Is Transient and Maintained by Tissue-Specific Class I Expression," *Transplantation Proceedings* 26:3314–3316 (1994).

Willis et al., "Type 1 Diabetes in Insulin–Treated Adult–Onset Diabetic Subjects," *Diabetes Res. Clin. Pract.* 42:49–53 (1998).

Yan et al., "Reduced Expression of Tap1 and Lmp2 Antigen–Processing Genes in the Nonobese Diabetic (NOD) Mouse Due to a Mutation in Their Shared Bidirectional Promoter," *J. Immunol.* 159:3068–3080 (1997).

TREATMENT OF AUTOIMMUNE DISEASE

CROSS REFERENCE TO RELATED APPLICATIONS

This application is a continuation-in-part of Ser. No. 09/521,064, filed on Mar. 8, 2000, which, in turn, claims benefit of U.S. provisional application Serial No. 60/123,738, filed on Mar. 10, 1999, both of which are hereby incorporated by reference.

BACKGROUND OF THE INVENTION

Early onset diabetes mellitus, or Type I diabetes, is a severe, childhood, autoimmune disease, characterized by insulin deficiency that prevents normal regulation of blood glucose levels. Insulin is a peptide hormone produced by the β cells within the islets of Langerhans of the pancreas. Insulin promotes glucose utilization, which is important for protein synthesis as well as for the formation and storage of neutral lipids. Glucose is also the primary source of energy for brain and muscle tissue. Type I diabetes is caused by an autoimmune reaction that results in complete destruction of the β cells of the pancreas, which eliminates insulin production and eventually results in hyperglycemia and ketoacidosis.

Insulin injection therapy has been useful in preventing severe hyperglycemia and ketoacidosis, but fails to completely normalize blood glucose levels. Although insulin injection therapy has been quite successful, it does not prevent the premature vascular deterioration that is the leading cause of morbidity among diabetics today. Diabetes-related vascular deterioration, which includes both microvascular deterioration and acceleration of atherosclerosis, can eventually cause renal failure, retinal deterioration, angina pectoris, myocardial infarction, peripheral neuropathy, and atherosclerosis.

A promising treatment for diabetes, islet transplantation, has been in human clinical trials for over ten years. Unfortunately, the results where Type I diabetes is the underlying etiology are poor. There have been many successes with islet transplantation in animals, but only where the animals are diabetic due to chemical treatment, rather than natural disease. The only substantiated peer reviewed studies using non-barrier and non-toxic methods and showing success with islet transplants in naturally diabetic mice use isogeneic (self) islets. The isogenic islets were transplanted into already diabetic NOD mice pre-treated with TNF-alpha (tumor necrosis factor-alpha); BCG (bacillus Calmette-Guerin, an attenuated strain of mycobacterium bovis); and CFA (complete Freund's adjuvant), which is an inducer of TNF-alpha (Rabinovitch et al., *J. Immunol.* (1997)159(12):6298–303). This approach is not clinically applicable primarily because syngeneic islets are not available. In the allograft setting of islet transplantation, the grafts are rejected presumably due to autoimmunity. Furthermore, diabetic host treatments such as body irradiation and bone marrow transplantation are too toxic in Type I diabetes patients, rendering the short-term alternative of insulin therapy more attractive.

I previously developed a transplant method to introduce allogeneic and xenogeneic tissues into non-immunosuppressed hosts, in which the cells are modified such that the donor antigens are disguised from the host's immune system (Faustman U.S. Pat. No. 5,283,058, hereby incorporated by reference). Generally, masked islets or transgenic islets with ablated class I are only partially protected from recurrent autoimmunity in spontaneous non-obese diabetic (NOD) mice (Markmann et al., *Transplantation* (1992) 54(6):1085–9). There exists the need for a treatment for diabetes and other autoimmune diseases that halts the autoimmune process.

SUMMARY OF THE INVENTION

The present invention provides a novel method for reversing existing autoimmunity.

Accordingly, the invention provides a method for increasing or maintaining the number of functional cells of a predetermined type (e.g., islet cells) in a mammal, involving the steps of: (a) providing a sample of cells of the predetermined type, (b) treating the cells to modify the presentation of an antigen of the cells that is capable of causing an in vivo autoimmune cell-mediated rejection response, (c) introducing the treated cells into the mammal, and (d) prior to, after, or concurrently with step (c) treating the mammal to kill or inactivate autoimmune cells of the mammal.

In preferred embodiments, step (b) involves eliminating, reducing, or masking the antigen, which is preferably MHC class I. Such methods are known, and are described, e.g., in Faustman, U.S. Pat. No. 5,283,058.

Preferably, step (d) involves administering to the mammal tumor necrosis factor-alpha ("TNF-alpha"), or a TNF-alpha inducing substance, (i.e., an agonist). As will be explained in more detail below, the TNF-alpha signaling pathway is an inflammatory pathway that effectively brings about killing of the autoimmune cells that attack the desired cells. There are many methods for stimulating TNF-alpha production, including the following: vaccination with killed bacteria or toxoids, e.g., BCG, cholera toxoid, or diphtheria toxoid; induction of limited viral infections; administration of LPS, interleukin-1, or UV light; activation of TNF-alpha producing cells such as macrophages, B-lymphocytes and some subsets of T-lymphocytes; or administration of the chemotatic peptide fMET-Leu-Phe; CFA-pacellus toxoid, Mycobaterium bovis bacillus, TACE (a metalloproteinase that mediates cellular TNF-alpha release), hydrozamates, p38 mitogen activated protein ("MAP") kinase, and viral antigens that activate $NF_\kappa B$ transcription factors that normally protect the cells from apoptosis (i.e., cell death).

Killing of undesired autoimmune cells can also be accomplished by administering agents that act as agonists for the enzyme, TNF-alpha converting enzyme, that cleaves the TNF-alpha precursor to produce biologically active TNF-alpha.

Autoimmune cells can also be killed by administering agents that disrupt the pathways that normally protect autoimmune cells from cell death, including soluble forms of antigen receptors such as CD28 on autoreactive T cells, CD40 on B cells that are involved in protection of autoimmune cells, and CD95 (i.e., Fas) on T-lymphocytes. Other such agents include p75NTF and lymphotoxin Beta receptor (LtbetaR).

The methods of the invention in some respects run counter to current treatment regimens for autoimmune diseases. Many of the major approved therapies for such diseases involve the administration of anti-inflammatory drugs that inhibit the production of TNF-alpha, including COX-2 inhibitors, and TNF antagonists. My studies indicate that these conventional therapies are actually deleterious, in that they bring about expansion of the population of harmful autoimmune cells in the patient, increasing the number and severity of lesions and autoreactive infiltrates. In addition, many of these anti-autoimmune inflammatory drug therapies cause severe re-bound disease after discontinuation. For example, treatment with anti-inflammatory agents actually increases the number of lymphocyte infiltrates in the pancreas of a diabetic. Once treatment is discontinued, these lymphocytes regain their normal function, resulting in a heightened autoimmune response.

The methods of the invention can be used to treat any of the major HLA class II-linked autoimmune diseases characterized by disruption in MHC class I peptide presentation and TNF-alpha sensitivity. These diseases include, for example, type I diabetes, rheumatoid arthritis, SLE, and multiple scelorosis. The method can be used in any mammal, e.g., human patients, who have early pre-symptomatic signs of disease, or who have established autoimmunity.

The invention also provides a method for increasing or maintaining the number of a predetermined type e.g., islet cells, in a mammal by the steps of (a) treating the mammal with an agent that kills or inactivates autoimmune cells of the mammal; (b) periodically monitoring the cell death rate of the autoimmune cells; and (c) periodically adjusting the dosage of the agent based on the information obtained in monitoring step (b).

In any of the methods of the invention in which TNF-alpha is administered or stimulated, two agents can be used together for that purpose, e.g., TNF-alpha and IL-1 can be used in combination therapy, as can any other combinations of agents.

In addition, the invention provides a method for diagnosing an autoimmune disease or predisposition to such a disease in a mammal (e.g., a human patient). The method includes the steps of (a) providing peripheral cells from a mammal; (b) treating these cells with a TNF-alpha treatment regimen and; (c) detecting cell death in the peripheral cells, where an increase in cell death, when compared with control cells, is taken as an indication that the mammal has an autoimmune disease or predisposition to such disease. This diagnostic method can be used for any mammal, however, the preferred mammal is a human patient. Peripheral cells that can be used in this method are, for example, splenocytes, T lymphocytes, B lymphocytes, or cells of bone marrow origin and in step (b) of the method, these cells are preferably treated with TNF-alpha.

By "functional cell," is meant cells that carry out their normal in vivo activity. In certain preferred embodiments of the invention, it is preferred that the cells are capable of expressing endogenous self peptide in the context of MHC class I.

By "predetermined type," when used in reference to functional cells, is meant that one may select a specific cell type. For example, one skilled in the art may decide to carry out the method of the present invention in order to increase or maintain the number of functional islet cells in the pancreas. In this example, the predetermined cell type is islet cells.

By "class I and peptide" is meant MHC class I presentation of peptide (i.e., self peptide) on the cell surface. Cytoplasmic antigens are believed to be processed into peptides by cytoplasmic proteases and at least in part by the proteasome, a multicatalytic proteinase complex of which the Lmp2 protein, discussed herein, is associated. The process of MHC class I presentation is thought to include formation of a complex between the newly synthesized MHC class I molecule, including a glycosylated heavy chain non-covalently associated with β2-microglobulin, and peptide within the rough endoplasmic reticulum of the cell. Thus, "class I and peptide" refers to the MHC class I/peptide complex as it is presented on the cell surface for education of the immune system.

By "killing" or "kills" is meant to cause cell death by apoptosis. Apoptosis can be mediated by any cell death pathway. According to the present invention, cells that are susceptible to killing are defective in protection from apoptosis due to a defect in a cell death pathway.

"Autoimmune cells," as used herein, includes cells that are defective in protection from apoptosis. This defect in protection from apoptosis can be in the pathway linked to TNF-induced apoptosis, or an apoptotic pathway unrelated to TNF. Autoimmune cells of the present invention include, for example, adult splenocytes, T lymphocytes, B lymphocytes, and cells of bone marrow origin, such as defective antigen presenting cells of a mammal.

By "defective" or "defect" is meant a defect in protection from apoptosis.

By "exposure" is meant exposure of a mammal to MHC class I and peptide (i.e., self peptide or endogenous peptide) by any means known in the art. In one preferred embodiment, exposure to MHC class I and peptide is carried out by administering to the mammal an MHC class I/peptide complex. In other preferred embodiments, exposure to MHC class I and peptide occurs by exposing the mammal to cells that express MHC class I and peptide.

By "cells capable of expressing MHC class I and peptide" is meant, for example, cells that are class I$^+$ or cells that are class I$^{-/-}$ (e.g., cells having a mutation in the $\beta_2$M gene) but that are reconstituted in vivo by a compensatory component (e.g., serum $\beta_2$M).

By "maintenance of normal blood glucose levels" is meant that a mammal is treated, for example, by insulin injection or by implantation of a euglycemic clamp in vivo, depending on the host being treated.

By "lmp2 gene or an equivalent thereof," is meant a cell that has a defect in prevention of apoptotic cell death, for example, a cell that has an ablation at a critical point in an apoptotic cell death pathway. In another aspect, "lmp2 gene or an equivalent thereof" means that a cell has a mutation in the lmp2 gene or a gene that carries out a function the same as or similar to the lmp2 gene (i.e., a gene encoding a proteasome subunit). Alternatively, the phrase "lmp2 gene or an equivalent thereof" can be used to refer to a cell that has a mutation in a gene that encodes a regulator of the lmp2 gene or another component of the proteasome complex. For example, a human homolog of the murine lmp2 gene is an equivalent of the lmp2 gene according to the present invention. As but another example, a gene that carries out the same or similar function as the lmp2 gene, but that has a low amino acid sequence similarity, would also be considered as an equivalent of the lmp2 gene according to the present invention.

"Combination therapy," or "combined therapy," as used herein, refers to the two-part treatment for increasing the number of functional cells of a predetermined type that includes both (1) ablation of autoimmune cells, and (2) re-education of the host immune system.

By "TNF-alpha induction," "TNF-alpha treatment regimen," or "TNF-alpha" includes the administration of TNF-alpha, agents that induce TNF-alpha expression or activity, TNF-alpha agonists, agents that stimulate TNF-alpha signaling, or agents that act on pathways that cause accelerated cell death of autoimmune cells, according to the invention. Stimulation of TNF-alpha induction (e.g., by administration of CFA) is preferably carried out prior to, after, or during administration (via implantation or injection) of cells in vivo.

By "effective," is meant that the dose of TNF-alpha, or TNF-alpha inducing agent, administered, increases or maintains the number of functional cells of a predetermined type in an autoimmune individual, while minimizing the toxic effects of TNF-alpha administration. Typically, an effective dose is a reduced dose, compared to doses previously shown to be ineffective at treating autoimmune disease, particularly established autoimmune disease.

The methods of the invention provide, for the first time, effective reversal of naturally-occurring (as opposed to chemically induced) mediated diseases such as type I diabetes.

Other features and advantages of the invention will be apparent from the following description of the preferred embodiment thereof, and from the claims.

DETAILED DESCRIPTION

Figure 1:
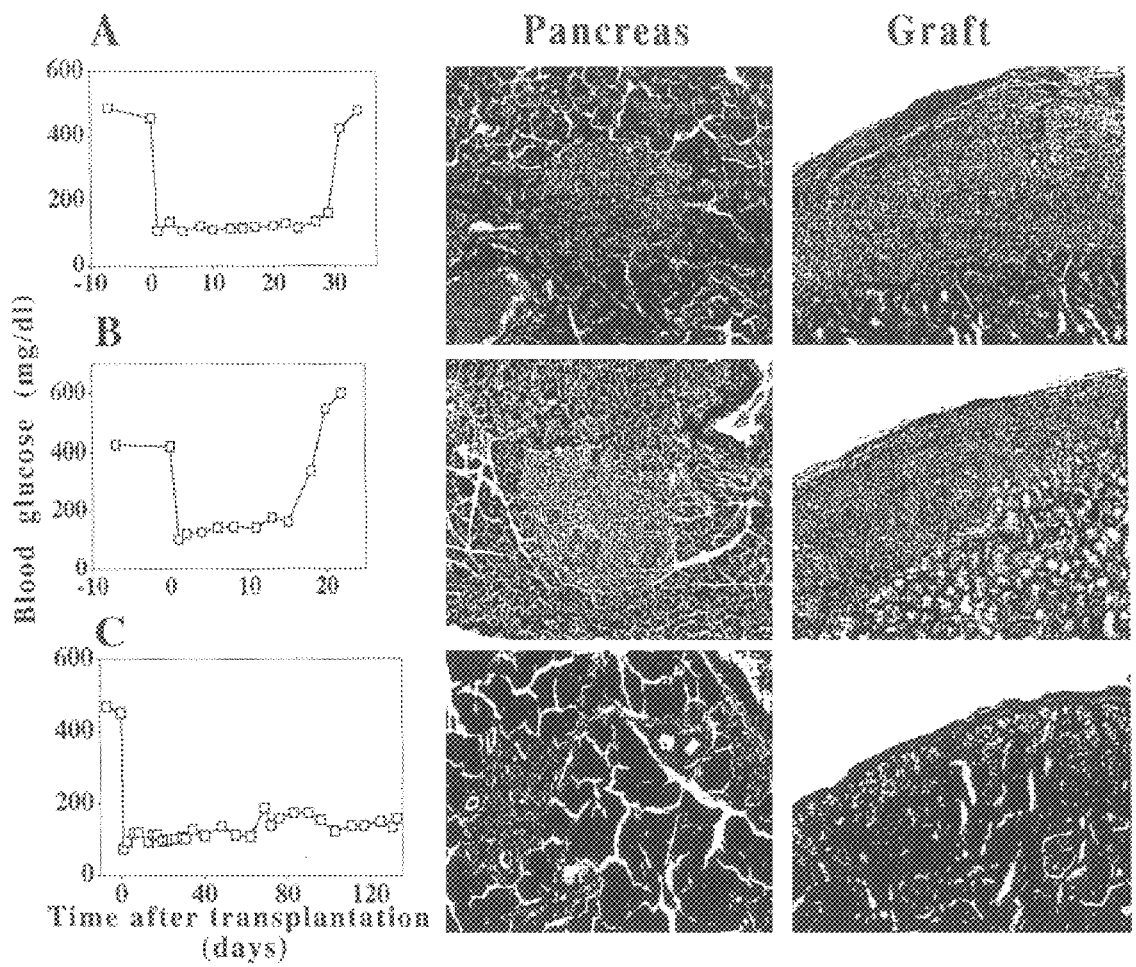
FIG. 1 shows three graphs that depict blood glucose concentration at indicated times after transplantation (left panels) and six photographs showing the histology of the pancreas (middle panels) and graft site under the kidney capsule (right panels) of diabetic NOD female mice subjected to transplantation with islets from various donor types and a single injection of CFA. Islet grafts were derived from young NOD mice (panel A), C57 mice (panel B), or $\beta_2M^{-/-}$ C57 mice (panel C).

The present invention provides a method of increasing or maintaining the number of functional cells of a predetermined type in a mammal by preventing cell death. In preferred embodiments, this method is used to treat an autoimmune disease where endogenous cell and/or tissue regeneration is desired. Such autoimmune diseases include, without limitation, diabetes melitus, multiple sclerosis, premature ovarian failure, scleroderm, Sjogren's disease, lupus, vilelego, alopecia (baldness), polyglandular failure, Grave's disease, hypothyroidism, polymyositis, pempligus, Chron's disease, colititis, autoimmune hepatitis, hypopituitarism, myocardititis, Addison's disease, autoimmune skin diseases, uveititis, pernicious anemia, hypoparathyroidism, and rheumatoid arthritis. One aspect of the invention provides a novel two-part therapeutic approach to ablate existing autoimmunity while re-educating the immune system via MHC class I and peptide. A key feature of the invention is the discovery that reexpression of endogenous antigens in the context of class I MHC is essential to terminate an ongoing autoimmune response.

As mentioned above, Type I diabetes results from destruction of the cells of the Islet of Langerhans of the pancreas via a severe autoimmune process. The goal for treatment of Type I diabetic patients is to permanently halt the gaff autoimmune process so that pancreatic islets are preserved. Alternatively, in cases where islet destruction from autoimmunity is complete, the goal is to provide a method of replacing islet cells, or allowing them to regenerate. Thus, the invention provides a novel method for increasing or maintaining the number of functional cells of a predetermined type for treatment of established cases of diabetes melitus, where existing autoimmunity is reversed.

In adult onset diabetes, or Type II diabetes, the β islet cells of the pancreas are often defective in secretion of insulin. However, recent studies indicate that, in some patients, autoimmune destruction of β islet cells does play an important role in disease progression (Willis et al., *Diabetes Res. Clin. Pract.* (1998) 42(1):49–53). Thus, the present invention may also be used to treat Type II diabetes where an autoimmune component is present.

Relating the Present Invention to Known Genetic and Functional Information

Genetic and functional studies have identified mutations in the lmp2 gene in NOD diabetic mice, a murine model for human type I diabetes (Li et al., *Proc. Natl. Acad. Sci., USA* (1994) 91:11128–32; Yan et al., *J. Immunol.* (1997) 159:3068–80; Fu et al., *Annals of the New York Academy of sciences* (1998) 842:138–55; Hayashi et al., *Molec. Cell. Biol.* (1999) 19:8646–59). Lmp 2 is an essential subunit of the proteasome, a multi-subunit particle responsible for processing a large number of intracellular proteins. The pronounced proteasome defect in Lmp2 results in defective production and activation of the transcription factor $NF_\kappa B$ through impaired proteolytic processing of $NF_\kappa B$ to generate $NF_\kappa B$ subunits p50 and p52 and impaired degradation of the $NF_\kappa B$ inhibitory protein, $I_\kappa B$. $NF_\kappa B$ plays an important role in immune and inflammatory responses as well as in preventing apoptosis induced by tumor necrosis factor alpha (TNF-alpha). Autoreactive lymphoid cells expressing the lmp2 defect are selectively eliminated by treatment with TNF-alpha, or any TNF-alpha inducing agent, such as complete Freund's adjuvant (CFA), or an agent that acts on a pathway required for cell death protection, for example, any pathway converging on the defective apoptotic activation mechanism. This is well illustrated by faulty apoptosis protection in the NOD mouse which lacks formation of protective $NF_\kappa B$ complexes.

The lmp2 gene is genetically linked to the MHC locus (Hayashi et al., supra). Antigen presenting cells of NOD mice cease production of LMP2 protein at approximately 5–6 weeks, a process that terminates the proper processing of endogenous peptides for display in the context of MHC class I on the cell surface. Surface display of endogenous peptide in the context of MHC class I molecules is essential for the selective elimination of T cells reactive to self antigens (Faustman et al., *Science* (1991) 254:1756–61; Ashton-Rickardt et al., *Cell* (1993) 73:1041–9; Aldrich et al., *Proc. Natl. Acad. Sci. USA* (1994) 91(14):6525–8; Glas et al., *J. Exp. Med.* (1994) 179:661–72). Current theory suggests that interruption of endogenous peptide presentation via MHC class I prevents proper T cell education and is responsible for a diverse array of autoimmune diseases (Faustman et al., supra; Fu et al., *J. Clin. Invest.* (1993) 91:2301–7). These data are also consistent with the clear sex-, tissue-, and age-specific differences in the expression of this error which parallel the initiation and disease course of insulin-dependent (type I) diabetes. It is hypothesized that the trigger for the initiation of autoimmunity is the tissue- and developmental-specific dysregulation of the proteasome (or MHC class I) in islet cells, as opposed to lymphocytes. As mentioned above, it is possible that this defect triggers a pathologic T cell response to islet cells via interruption of proper T cell education (Hayashi et al., supra).

In a normal, non-diabetic, human or animal, peripheral tissues, including islets, consistently express endogenous antigens in the context of MHC class I (Hayashi et al., supra). Constitutive tissue-specific display of self peptide via MHC class I could maintain peripheral tolerance in the context of properly selected lymphocytes (Vidal-Puig et al., *Transplant* (1994) 26:3314–6; Markiewicz et al. *Proceedings of the National Academy of Sciences of the United States of America* (1998) 95(6):3065–70). In the absence of such tissue-specific display, poor negative selection of T-lymphocytes could lead to overexpansion of self-reactive lymphocytes, a prominent feature in human and murine disease models.

As mentioned above, autoreactive lymphoid cells expressing the lmp2 defect are selectively eliminated, for example, by treatment with TNF-alpha, or any TNF-alpha inducing agent, such as complete Freund's adjuvant (CFA). Although the specific gene defect has not been identified in human autoimmune patients, it is known that human splenocytes in the human diabetic patient, like murine splenocytes in the NOD mouse, have defects in resistance to TNF-alpha induced apoptosis (Hayashi et al., supra). Specific cells in human autoimmune patients might express a genetic defect, similar to the proteasome defect in mice, that increases susceptibility to TNF-alpha induced apoptosis or an analogous apoptotic cell death pathway. Therefore, in patients expressing the genetic defect, only the autoimmune cells are killed. Permanently eliminating the autoreactive cells is a key feature of an effective treatment for an autoimmune disease.

According to the present non-limiting theory, of the invention, multiple cell death pathways exist in a cell and any one or more of these cell death-related pathways may be defective, accentuating the sensitivity of these cells to cell death. For example, susceptibility to TNF-alpha induced apoptosis could occur via a failed cell death inhibition pathway (e.g., by defective production and activation of the transcription factor $NF_\kappa B$, as in the NOD mouse). Further, it is well known that there are two different TNF-alpha receptors. Defective signaling through either receptor could render autoimmune cells susceptible to TNF-alpha induced apoptosis. As but another example, defective cell signaling through surface receptors that stimulate pathways that interact with the cell death pathway, i.e., LPS, IL-1, TPA, UV light etc., could render autoimmune cells susceptible to apoptosis according to the theory of the present invention. Therefore, methods of the present invention that are beneficial in the treatment of autoimmune disease are applicable to any autoimmune patient that has a defect in a cell death pathway.

As mentioned above, current therapies for autoimmune disease are directed toward decreasing the inflammatory reaction that is thought to be responsible for destruction of self. TNF-alpha is part of the inflammatory response. Thus, according to the present theory, induction of an inflammatory response, rather than inhibition of an inflammatory response, is the preferred method of treating an autoimmune individual. This theory runs counter to existing dogma surrounding autoimmune therapy today.

It is possible that TNF-alpha is inducing a cytokine, toxoid, or other related molecule induced in the inflammatory response that is the responsible for the benefit of TNF-alpha treatment. If so, induction of inflammation via TNF-alpha treatment is still in agreement with the theory of the invention. In a preferred embodiment, induction of inflammation via TNF-alpha treatment induces mediators of autoimmune cell death.

A Novel Assay for Monitoring Treatment

It is well known that prolonged TNF-alpha treatment by itself is highly toxic. In light of the elucidation of the cell death pathway described above, we hypothesized that the knowledge of this pathway could enable development of a sensitive in vitro assay that could be used to monitor the in vivo effect of a particular TNF-alpha treatment regimen (i.e., any treatment regimen that results in induction of TNF-alpha and inflammation). More particularly, a monitoring system could be developed that combined the administration of TNF-alpha alone with an assay capable of measuring the effect of TNF-alpha treatment on apoptosis of autoimmune cells in a mammal diagnosed with an autoimmune disease. Such a monitoring system would make it possible to measure the effect of particular doses of TNF-alpha on the apoptosis of autoimmune cells concurrently with treatment of an autoimmune individual. Moreover, such a monitoring system would enable optimization or adjustment of the dose of TNF-alpha (i.e., or TNF-alpha inducing agent) to maximize autoimmune cell death, while minimizing exposure of the mammal to toxic doses of TNF-alpha.

Thus, the invention provides a method of increasing or maintaining the number of functional cells of a predetermined type in a mammal that involves a) treating a mammal to kill or inactivate autoimmune cells of the mammal; b) periodically monitoring the cell death rate of the autoimmune cells (i.e., by assaying the cell death rate of autoimmune cells in the mammal, wherein an increase in cell death rate of auto reactive T-lymphocytes indicates an increase in the number of functional cells of the predetermined type (i.e., resistant to cell death)); and (c) periodically adjusting the dosage of the agent based on the information obtained in step (b). The autoimmune cells of the present invention include any cell defective in protection from apoptotic cell death by any stimulus, for example, TNF-alpha, CD40, CD40L, CD28, IL1, Fas, FasL, etc.

The assay of step (b) allows one to identify novel formulations of TNF-alpha, TNF-alpha inducing agents, TNF-alpha agonists, or agents that act on the TNF-alpha signaling pathway effective in inducing apoptosis of T-lymphocytes or antigen presenting cells, that can be administered over a longer course of treatment than was possible prior to the present invention (e.g., preferably over a period of months, more preferably over a period of years, most preferably over a lifetime).

In a related embodiment, the present monitoring system may be used to identify new doses, durations of treatment, and treatment regimens for TNF-inducing agents that were previously discounted as useful treatments because there was no way to monitor their effect. For example, in contrast to a preliminary report identifying BCG, a TNF-alpha inducing agent, as a useful type I diabetes treatment (Shehadeh et al., *Lancet*, (1994) 343:706), researchers failed to identify a therapeutic dose of BCG because there was no way to monitor the effect of BCG in vivo (Allen et al., *Diabetes Care* (1999) 22:1703; Graves et al., *Diabetes Care* (1999) 22:1694).

The assay of step (b) may also be used to tailor TNF-alpha induction therapy to the needs of a particular individual. For example, as mentioned above, in one preferred embodiment, the assay of step (b) can be carried out every day or every other day in order to measure the effect of TNF-induction therapy and/or cell death inducing agents on autoimmune cell death rate so that adjustment to the administered dose, duration of treatment (i.e., the period of time over which the patient will receive the treatment), or treatment regimen (i.e., how many times the treatment will be administered to the patient) of TNF-alpha can be made to optimize the effect of TNF-alpha treatment and minimize the exposure of the patient to TNF-alpha or other cell death inducing agents. Of course, the skilled artisan will appreciate that the assay can be performed at any time deemed necessary to assess the effect of a particular regimen of TNF-alpha induction therapy on a particular individual (i.e., during remission of disease or in a pre-autoimmune individual).

The assay can be used to tailor a particular TNF-alpha induction regimen to any given autoimmune disease. For example, the in vitro monitoring of selective killing of autoimmune cells can be used to selectively grade the drug (i.e., adjust the dose administered to maximize the therapeutic effect). The monitoring system described herein can be used to monitor in vivo trials of TNF-alpha treatment by continuously measuring the elimination of autoimmune cells, e.g., autoreactive T lymphocytes, with continuing sensitivity. Of course, the skilled artisan will appreciate that the present monitoring system can be used to measure the effect of TNF-alpha on in vivo killing of autoimmune cells in cases where TNF-alpha-induction therapy is cited in conjunction with any other therapy, e.g., T cell re-education, as described herein.

It is well known that TNF-alpha induction therapy has been shown to be ineffective in patients with established autoimmunity, e.g., established diabetes, but is effective in patients in a pre-autoimmune state, e.g., patients in a pre-diabetic or pre-lupus state. In addition, it has been established that TNF-alpha induction in adult NOD and NZB mice (a murine strain susceptible to lupus-like disease) decreases diabetic or lupus symptoms respectively. According to the invention, TNF-alpha therapy can be effective even in patients with established disease, by monitoring the elimination of autoimmune cells and optimizing the dose, duration of treatment, and/or re-treatment schedule accordingly. Thus, the assay of step (b) may be used to identify an effective dose, duration of treatment, or treatment regimen of TNF-alpha (e.g., lower than doses previously shown to be ineffective in treatment of diabetes, particularly in the treatment of established diabetes) that can be used as an effective treatment for autoimmune disease.

In another preferred embodiment, the assay of step (b) is used to identify a dose, duration of treatment, or treatment regimen of TNF-alpha that can reduce or eliminate side effects associated with a particular autoimmune disease. A particular dose of TNF-alpha may be identified that reduces or eliminates the symptoms associated with, for example, vascular collapse associated with diabetes, blindness or kidney failure associated with Type 1 diabetes, or skin eruptions associated with lupus. It is well established that it is the side effects associated with the autoimmune reaction that are often responsible for mortality of autoimmune patients. Thus, in one preferred embodiment, the monitoring system of the present invention identifies a treatment regimen for TNF-alpha that reduces the symptoms and/or complications of the autoimmune disease, such that the quality of life of the patient is improved and/or the life-span of the patient being treated is prolonged. In a related embodiment, the monitoring system of the present invention identifies a treatment regimen for TNF-alpha that prevents disease progression or even halts disease in a patient diagnosed with an autoimmune disease.

Thus, in another aspect, the present invention provides a monitoring system for measuring the rate of cell death in an autoimmune mammal, including (a) a treatment regimen for killing or inactivating autoimmune cells in a mammal; and (b) an assay capable of measuring the effect of the treatment regimen on the cell death rate of autoimmune cells in the mammal, wherein an increase in cell death rate indicates an decrease in autoimmunity.

In Vitro Assay for Monitoring Cell Death

The present invention provides a novel assay for monitoring apoptosis of autoimmune cells in a mammal. In one preferred embodiment, the present invention provides an assay involving (a) isolating a blood sample from a mammal, preferably a human, and (b) testing the blood sample in vitro for killing of autoimmune cells compared to non-autoimmune cells using techniques available in the art. As mentioned above, non-autoimmune cells are generally resistant to TNF-alpha induced apoptosis. An increase in cell death in autoimmune cells compared to non-autoimmune cells indicates that the dose of TNF-alpha or other cell death inducing agent is sufficient to induce killing of the autoimmune cells or defective bone marrow origin cells.

Combined TNF Induction Therapy

The present invention also features a drug combination that includes two or more TNF-alpha inducing agents. One particularly preferred combined TNF-alpha treatment is the combination of TNF-alpha and IL1. This treatment strategy goes against the current dogma surrounding treatment of autoimmune disease. For example, at the TNF Second International Meeting (A Validated Target with Multiple Therapeutic Potential, Feb. 24–25, 1999, Princeton, N.J., USA) it was disclosed that a combination of anti-TNF-alpha antibody and anti-IL1 would be advantageous in the treatment of autoimmune disease. The treatment of the present invention discloses induction of inflammation, which is the opposite of the treatment believed to be effective by those skilled in the art, that is, suppression of inflammation. Of course, in the current treatment, inflammation does not occur because the inflammatory cells actually die prior to arriving at the target site or are killed at the target site.

Of course, the present invention is not limited to a combined TNF inducing therapy that includes only the combination of TNF-alpha and IL1, but includes any combination of TNF-alpha-including therapies, e.g., vaccination with BCG etc., viral infection, LPS, activation of cells that normally produce TNF-alpha (i.e., macrophages, B cells, and T cells), the chemotactic peptide fMet-Leu-Phe, bacterial and viral proteins that activate $NF_\kappa B$, agents that induce signaling pathways involved in adaptive immune responses (i.e., antigen receptors on B and T cells, CD28 on T cells, CD40 on B cells), agents that stimulate specific autoreactive cell death receptors (i.e., TNF, Fas (CD95), CD40, p75NF, and lymphotoxin Beta-receptor (LtbetaR), drugs that stimulate TNF-alpha converting enzyme (TACE) which cleaves the TNF-alpha precursor (i.e., to provide biological activity capable of stimulating enhanced production or enhanced cytokine life after secretion) etc.

Identification of Inflammation-inducing Agents

In preferred embodiments, the present invention provides inflammatory agents for the treatment of autoimmune disease that are counter to the anti-inflammatories used to treat autoimmune diseases today. For example, current methods for treating autoimmune disease include TNF-alpha antagonists. Thus, the present invention provides TNF-alpha agonists (i.e., chemicals, peptides, or antibodies) that act on a TNF-alpha receptor. Other preferred treatments could fall under the categories of drugs that act in opposite to anti-TNF-alpha agonists, anti-TNF-alpha antibodies, TNFR2 fusion proteins (Immunex), Embrel, anti-IL1 therapies, TNF-alpha convertase inhibitors, p38 MAP kinase inhibitors, phoshodiesterase inhibitors, thalidomide analogs, and adenosine receptor agonists.

In another preferred embodiment, the invention allows for the identification of drugs that induce cell death or selectively hamper the autoimmune cells by binding to cell surface receptors or interacting with intracellular proteins. For example, drugs that stimulate the IL-1 pathway or drugs that interact with converging pathways such as Fas, FasL, TACI, ATAR, RANK, DR5, DR4, DCR2, DCR1, DR3, etc. The drugs of the present invention can be characterized in that they only kill autoimmune cells having a selective defect in a cell death pathway which can be characterized by two distinct phenotypes, (1) defects in antigen presentation for T cell education and (2) susceptibility to apoptosis.

It will be appreciated that the above-described assay for monitoring death of autoimmune cells can be used to identify novel TNF-alpha inducing agents and other inflammatory agents useful in the present invention. In preferred embodiments, autoimmune cells (i.e., an autoimmune cell isolated from a mammal diagnosed with autoimmune disease) are exposed to a putative inflammatory or TNF-alpha inducing agent and assayed for increased cell death, an increase in cell death of autoimmune cells compared to non-immune cells indicating identification of a drug according to the present invention. Furthermore, autoimmune blood could be exposed to chemical libraries for preferred and selective cell death of yet unknown targets compared to non-autoimmune cells. A wide variety of chemical libraries are available in the art and can be screened by use of the assay of the invention, which measures the rate of apoptosis of autoimmune cells.

In a related aspect, the above-described assay for monitoring death of autoimmune cells can be used to identify autoimmune cells having the two distinct phenotypes described above. In contrast to typical genetic approaches for identifying cells carrying genetic defects, sensitivity to cell death may serve as the initial identification marker. Once cell-death sensitive cells are identified, they can be assessed as to whether they also have the class I antigen presentation defect. Thus, the present invention provides a method of identifying autoimmune cells by (1) assaying the cells for a susceptibility to apoptosis and (2) assaying for defects in antigen presentation required for T cell education.

A Novel Combination Therapy

The data presented in Table 1 and described in detail in Example 1, below, demonstrate the remarkable success of combining two methods to induce long-term normoglycemia with islet allograft transplantation in an already diabetic NOD host. The invention combines two therapies aimed at two separate targets of the immune system. The invention tests this concept by combining my prior transplantation technology with an autoimmune strategy to thwart the underlying disease, and for the first time provides long-term normoglycemia in naturally diabetic hosts via transplantation with allogeneic islets. Thus, the invention, views the rejection problem as one involving two immune barriers, i.e., the graft rejection barrier and the recurrent autoimmunity barrier. To address the graft rejection barrier, I used donor antigen modified islets, and for the recurrent autoimmune barrier I used CFA, a strong inducer of TNF-alpha.

TABLE 1

| Groups | Donor Strain | Host Strain | Treatment | Individual Survival (days) Days of normoglycemia | Mean |
|---|---|---|---|---|---|
| 1. | C57BL/6 | NOD-IDDM* | — | 2, 2, 3, 9, 23 | 7.8 |
| 2. | $\beta_2M^{-/-}$ | NOD-IDDM | — | 5, 9, 12, 12, 17, 18, 71 | 20. |
| 3. | C57BL/6 | BALB/C | — | 5, 5, 7, 10 | 6.7 |
| 4. | $\beta_2M^{-/-}$ | BALB/C | — | >100, >100, >100, >100 | >100 |
| 5. | NOD | NOD-IDDM | — | 5, 10, 12, 13 | 10 |
| 6. | NOD | NOD-IDDM | CFA | 12, 26, 30, >38, >66, >120, >122 | >59 |
| 7. | C57BL/6 | NOD-IDDM | CFA | 10, 10, 10 | 10 |
| 8. | $\beta_2M^{-/-}$ | NOD-IDDM | CFA | 5, 14, 32, 36, >59, >79, >115, >115 | >57 |

*IDDM stands for insulin-dependent diabetes melitus.

Table 1, above, represents a series of experiments that were carried out in which host mice were treated to prevent recurrent autoimmunity, via killing or inactivation of autoreactive lymphocytes, and then transplanted with donor islet cells in which rejection triggering antigens had been eliminated or modified.

The mice were injected once intraperitoneally with complete Freund's adjuvant (CFA) (25 µl/mouse) to induce TNF-alpha.

The same day, islet cell transplantation was carried out as follows. The donor antigen modified islet cells were isolated from transgenic $\beta_2M$ ($\beta2$ microglobulin) knockout mice purchased from the Jackson Labs. As mentioned above, the $\beta_2M$ gene encodes a critical chaperone protein essential for surface expression of class I proteins. Host $\beta_2M$, a highly conserved protein, can in part re-constitute $\beta_2M$.

Transgenic or normal islet cells were transplanted into nine groups of mice. Three of the groups (groups 6, 7, and 8) were pre-treated with CFA; the other six groups were not pre-treated.

As is shown in Table 1, naturally diabetic mice (NOD-IDDM) that received transgenic transplants but were not pre-treated with CFA (group 2) had mean survival times of 20 days, suggesting that the protection of donor tissue from graft rejection does not protect the tissue from an established autoimmunity. Likewise, group 7 establishes that host treatment with CFA, an immunomodulator now believed to modify exclusively the autoimmune response, does not protect normal allogeneic donor cells from rapid graft rejection. In contrast, the CFA treated diabetic mice receiving transgenic transplants (groups 6 and 8) survived over 57 days (mean). The remaining groups were additional controls: group 1 (no CFA; diabetic host, non-transgenic donor cells); group 3 (no CFA; non-diabetic host, non-transgenic donor cells); group 4 (no CFA; non-diabetic host; non-transgenic donor cells); and group 7 (CFA; diabetic host; non-transgenic donor strain). As is shown in Table 1, the only one of these control groups exhibiting longevity were non-diabetic hosts receiving transgenic donor cells, a therapy known to thwart graft rejection (group 4).

At approximately 120–130 days post transplantation, the transplanted syngeneic and allogeneic islets were removed by nephrectomy. This was a control experiment to prove the animals reverted back to hyperglycemia.

The NOD mice receiving the syngeneic transplant had, within 24 hrs, blood sugars in excess of 500 mg/dl and needed to be sacrificed immediately because of their severe diabetic state. Histology on these mice showed that the transplanted islets in the kidney survived in some cases but did not appear, in all cases, healthy. There were granulated islets, but massive lymphocytic infiltrates surrounded and invaded the islet tissue. The islet invasion by host lymphocytes is a histologic trait indicative of autoreactivity against the islet tissue. The endogenous pancreas demonstrated no surviving islets and was dotted with large lymphocytic clusters, presumably at sites of former islet tissue.

The NOD mice receiving the allogeneic islets, in contrast, remained normoglycemic after the nephrectomies had been performed to remove the allogeneic islet tissue. No change in blood sugar was noted. After approximately seven days of this perfect blood sugar control, the mice were sacrificed. Histologic examination showed that endogenous islets in the pancreas were regenerated. The islet number was less than normal, but the islets present were large, healthy, and had no lymphocyte invasion (although they did have a characteristic NOD rim of lymphocytes surrounding the healthy islet). In contrast, the allogeneic grafts were gone in most cases by this late 120–140 day post-transplantation time point. These results support the thesis that what occurred was rescue and regeneration of the endogenous pancreas. The results support that the immune system was additionally re-educated.

Thus, in one preferred embodiment, the invention provides a method of inhibiting rejection of transplanted islet cells in a diabetic patient, by (a) pre-treating the islet cells to modify, eliminate, or mask islet cell antigen otherwise capable of causing T-lymphocyte-mediated rejection response in a patient, together with (b) treating the patient (prior to, during, or following transplantation) to kill or inactivate autoreactive host lymphocytes that are otherwise capable of killing or damaging the transplanted islet cell.

In preferred embodiments, step (a) involves genetically altering the donor animal so that HLA class I or a molecule in its pathway is genetically deleted or chaperone ablated to prevent surface expression, or masking HLA class I antigen using an antibody F (ab')$_2$ fragment that forms a complex with HLA class 1; and step (b) involves administering to a patient TNF-alpha, or a TNF-alpha inducing substance, e.g., tissue plasminogen activator (TPA), LPS, IL-1, TV light, such as an interacellular mediator of the TNF-alpha signaling pathway or an inducer of cell death in defective cells.

Class I Antigen Presentation

Prior to the experiments described above, I observed that a small amount of class I ablation was beneficial for the inhibition of rejection of donor islets in diabetic NOD mice (Faustman et al., Science (1991) 252(5013):1700–2). Based on these results, I proposed that a more complete and permanent class I ablation might even be better for long term graft survival. To achieve a more permanent class I ablation, I transplanted F2 islets that were ablated for both the $\beta_2M$ ($\beta2$ microglobulin) gene and Tap 1 into already diabetic NOD mice (MHC class I$^{-/-,--}$) (see Example 3). The $\beta_2$M gene encodes a critical chaperone protein essential for surface expression of class I peptides. The Tap 1 gene encodes a protein required for transport of endogenous self-peptides into the endoplasmic reticulum for stable peptide and class I assembly before presentation on the cell surface. Surprisingly, only one of the six mice exhibited long term graft survival. Individual graft survival times (days) for the six mice were: 11, 12, 13, 14, 14, and 71. These unexpected results suggested that the reexpression of peptide and class I was a step that was not only not harmful, but was actually necessary for immune system re-education leading to endogenous islet regeneration and rescue. Thus, in the present application, I propose, without limiting the biochemical mechanism of the invention, that some intact MHC class I molecules are required for the re-education process to occur.

Based on the above-described results, it appears that the graft rejection barrier actually serves two important functions that appear to contribute to successful islet cell regeneration in this model. Temporary class I ablation (class I$^{-/-}$) serves initially to protect the graft from immediate rejection. Subsequently, MHC class I proteins are reexpressed and exchanged on the graft by 24–72 hours post-transplantation through abundant host $\beta_2$M proteins from the serum (Anderson et al., *J. Immunol.* (1975) 114(3):997–1000; Hyafil et al., *Proc. Natl. Acad. Sci., USA* (1979) 76(11):5834–8; Schmidt et al., *Immunogenetics* (1981) 13:483–91; Bernabeu et al., *Nature* (1984) 308(5960):642–5; Li et al., *Transplantation* (1993) 55(4):940–6). Surprisingly, subsequent reexpression of endogenous peptide via MHC class I appears to contribute to the reeducation of T lymphocytes with proper negative selection of autoreactive cells. In further support of this observation, I demonstrated, that to be therapeutically effective, at least one MHC class I K or D locus of the donor lymphocytes needed to be matched to the corresponding locus in the NOD host mouse (i.e., either the $K^d$ or $D^b$ locus should be present on the donor MHC class I expressing cells). Therefore, the reeducation component of the combination therapy requires that the MHC class I expressing cells, presenting the self-peptide, be semi-syngeneic or fully syngeneic to the autoreactive cells in the NOD host mouse. Coupled with the selective elimination of autoreactive lymphoid cells by treatment with CFA, the present combination therapy provides a powerful treatment for autoimmune disease where regeneration of tissue is desired.

Maintenance of Transplanted Islet Cells is not Required for Regeneration of Endogenous Pancreas The experiments described above further suggested to me that maintenance of the transplanted islets in vivo might not be necessary for endogenous pancreatic islet cell regeneration. In order to test this theory, transgenic MHC class I$^{-/-}$ islet grafts were transplanted into already diabetic NOD mice with TNF-alpha induction. Transgenic MHC class I$^{-/-}$ islet grafts placed under the kidney of diabetic NOD mice were later removed by nephrectomy at various times post-transplantation. As described in Example 2, all mice remained normoglycemic for at least 120 days after nephrectomy and the pancreatic histology revealed beautiful endogenous pancreatic islet regeneration. In contrast, NOD mice that received syngeneic islet transplants rapidly returned to hyperglycemia post-nephrectomy.

As proposed above, these data support the theory that for endogenous regeneration of islets, or other regenerating tissue subject to immune attack (e.g., hepatic cells), maintenance of the transplanted islet cells is not essential to endogenous pancreatic islet cell regeneration and rescue. Thus, the invention, in one respect, views the problem of tissue regeneration and rescue in autoimmunity as one involving two different barriers, (i.e., the recurrent autoimmunity barrier and the re-education barrier). The required steps for tissue regeneration appear to be: (1) ablate the host autoimmune cells (e.g., by killing or inactivation); and (2) re-educate the immune system with class I and peptide to protect the regenerating pancreas.

Thus, the present invention provides a method of reestablishing systemic tolerance and eliminating existing autoimmunity that promotes regeneration and rescue of cells and tissue.

Treatment by Injection of MHC Class I and Peptide

Based on the discovery that class I peptide presentation is required for re-educating the NOD host and the knowledge that maintenance of transplanted islet cells is not required for endogenous islet cell regeneration, I proposed that islet transplantation and isolation might not be necessary for in situ islet regeneration in setting of autoimmunity. Islet isolation and transplantation are laborious procedures with associated supply and demand limitations in the clinical setting. A procedure for increasing the number of functional islet cells that does not require islet isolation and transplantation would provide great benefit to the treatment of diabetes. This method of treatment could be extended to other autoimmune diseases where immune reeducation is desired (U.S. Pat. No. 5,538,854).

I proposed that mere injection of functional cells expressing class I (class I$^+$), or even MHC class I/peptide complex, into a mammal, with concurrent ablation of autoimmune cells, would be efficacious in treating a diverse array of autoimmune diseases. For example, normal pancreatic islets express MHC class I and have few associated passenger lymphocytes that express both MHC class I and class II molecules (this preparation is referred to herein as B6 splenocytes). In the case of diabetes, a preparation of normal pancreatic islet cells may be injected into a patient to achieve exposure to class I antigen. Although donor cell survival may be short lived, repeated exposure might be sufficient to re-educate the host immune system with concurrent ablation of autoimmune cells. In cases where donor cell preparation is tedious or poor donor cell survival time is limiting the efficacy of the method, class I/peptide complex may be administered directly to the host.

In order to test this hypotheses, diabetic NOD mice were initiated on a 40 day regimen of one bolus injection of CFA to transiently induce TNF-alpha and biweekly exposure by intravenous injection to B6 splenocytes (class I$^+$) (Example 4). As predicted, the injected splenocytes survived only transiently in the host due to rejection. However, transient elimination of autoimmune cells (e.g., via CFA-mediated TNF-alpha induction) combined with repeat exposure to B6 MHC class I and peptide was sufficient for reversal of diabetes in approximately 30% of diabetic NOD hosts. Partial protection was achieved in approximately 50% of the diabetic NOD hosts, but the percentage of host NOD mice remaining normoglycemic increased to 80% after allowing the islets to regenerate for more than 120 days. Furthermore, since the donor B6 splenocytes have a MHC class I phenotype of $K^b D^b$ and the host NOD mice have a MHC class I phenotype of $K^d D^b$, I was able to determine that the now normoglycemic host NOD mice had insulin secreting pancreatic cells of donor B6 origin, based on $K^b$ antibody staining. In addition, to support this finding, I determined that only injection of live, non-irradiated, splenocytes resulted in a contribution of the donor MHC class I phenotype to the host insulin secreting cells.

Figure 5:
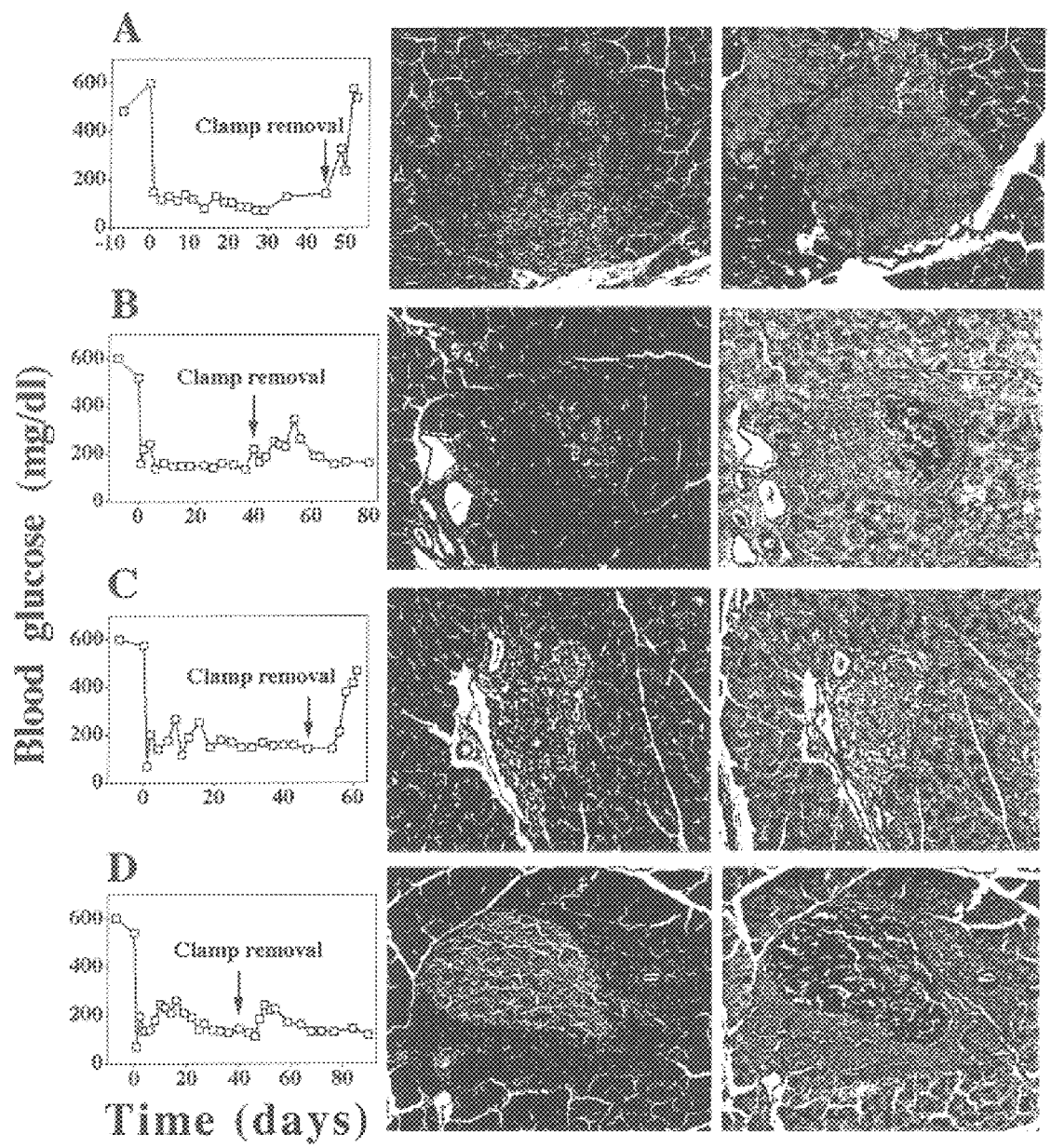
FIG. 5 shows four graphs (left panel) that depict the effect of maintenance of normoglycemia during TNF-alpha induction and splenocyte treatment on islet regeneration in diabetic NOD mice. The graphs are accompanied by eight photographs that show the histology of the pancreas, specifically islets and associated lymphocytic infiltrates (middle panels) and islet insulin content (right panels). Arrows represent time of removal of euglycemic clamp. Mice received a single injection of CFA only (panel A), CFA plus biweekly injections of splenocytes ($9 \times 10^6$) from normal C57 mice (panel B), $\beta_2M^{-/-}$, TAP1$^{-/-}$ C57 mice (panel C), or MHC class II$^{-/-}$ C57 mice (panel D).

Blood sugar levels were poorly controlled in mice receiving the injection therapy described above. Fluctuations in blood sugar level could negatively influence benefit of the combined injection therapy. In order to control for this variant, additional groups of diabetic NOD mice were similarly treated with TNF-alpha induction and B6 splenocyte injection, but with simultaneous intraperitoneal implantation of B6 islets encapsulated with alginate (referred to herein as a euglycemic clamp). A euglycemic clamp provides a membrane barrier system that allows short term glycemic control of insulin exchange but prevents direct cell-cell contact (e.g., for T cell education). After 40 days, the encapsulated islets were surgically removed and blood sugar levels of the diabetic NOD mice were monitored for evidence of in situ pancreas regeneration. Remarkably, diabetic NOD mice that had received biweekly B6 splenocyte immunizations and a single dose of TNF-alpha induction therapy remained normoglycemic for 40 days after clamp removal in 78% of the cases. Moreover, after the therapy was halted and autoimmunity eliminated, the continuous expansion of the endogenous pancreas was sufficient for sustained tolerance to self antigens. In contrast, in control experiments, where splenocytes permanently ablated for MHC class I proteins (MHC class $I^{-/-,-/-}$), poor in situ islet regeneration was observed (Table 3, group 4, FIG. 5). However, injection of splenocytes lacking MHC class II proteins (MHC class $II^{-/-}$) permitted in situ islet regeneration, presumably due to continued expression of endogenous peptide in the context of MHC class I (Table 3, group 5, FIG. 5). Therefore reestablishment of self tolerance and elimination of autoreactivity was MHC class I dependent.

Therefore, I have identified and optimized a novel combination treatment for diabetes melitus. Thus, in yet another aspect, the present invention features a method of increasing and preserving the number of functional cells of a predetermined type in a diabetic patient that includes the steps of (1) ablation of autoimmune cells, (2) exposure to MHC class I and peptide, and (3) maintenance of glucose control. As mentioned above, exposure may occur, for example, either by transplantation of functional MHC class I and peptide presenting cells of a predetermined type, or preferably by repeated injection of such cells. Alternatively, exposure to MHC class I and peptide may occur by injection of class I/peptide complexes, peptide feeding of autologous cells etc.

In a particularly preferred embodiment, the present invention provides a method of increasing the number of functional cells of a predetermined type in a diabetic patient that includes the steps of (1) ablation of autoimmune cells (i.e., cells that are defective in cell death), (2) exposure to MHC class I and peptide by repeated injection of functional cells of a predetermined type, expressing peptide in the context of MHC class I (or MHC class I/peptide complex), and (3) maintenance of glucose control. In the case of diabetes, the functional cells of a predetermined type include islet cells, for example, B6 splenocytes. Maintenance of blood glucose levels may be achieve by any means known in the art, for example, insulin injection, or by use of a euglycemic clamp. The diabetic patient can be any mammal, preferably a human patient.

Treatment of Autoimmune Disease

Based on the discoveries described herein, I have devised a novel therapy for the correction of any established autoimmunity. Used in combination, exposure to self peptide in the context of MHC class I and killing or inactivation of autoreactive lymphocyte permits the endogenous regenerative potential of mammalian tissue to be enacted. In addition, the present treatment enables preservation and rescue of existing tissue. The effect of this combination therapy is the re-education of the immune system with the simultaneous reversal of autoimmunity within the host.

With respect to diabetes treatment, I further hypothesize that successfully regenerated pancreatic B6 islet cells that hyper-express MHC class I and peptide (e.g., determined by histological examination) maintain peripheral tolerance once sufficient islet growth has been established. In vivo exposure to MHC class I and peptide expressing cells by transplantation or injection appears to initiate the educational process for long-term and stable tolerance, beyond the period of treatment.

Several striking similarities exist between the NOD mouse and human diabetic patients, suggesting that this novel therapeutic approach can be easily applied to treat human diabetic patients. For example, diabetic human splenocytes, like murine splenocytes, have defects in resistance to TNF-alpha induced apoptosis (Hayashi et al., supra). In addition, like NOD mice, human splenocytes have age related defects in MHC class I presentation of self peptides for proper T cell selection (Faustman et al., supra; Fu et al., *J. Clin. Invest.* (1993) 91:2301–7). Finally, it has been recognized for years that even after a severe hyperglycemic episode, diabetic humans continue to produce autoantibodies to islet targets, indicating that the islet cells or islet precursor cells of the pancreas were not completely ablated. This indicates that humans diagnosed with diabetic autoimmunity may have high islet regenerative potential.

Thus in one aspect, the invention features a method of increasing the number of functional cells of a predetermined type in an individual diagnosed with an autoimmune disease, by (1) providing a sample of functional cells expressing MHC class I and peptide, (b) exposing a mammal to the MHC class I and peptide, and (c) prior to, after or concurrently with step (b), treating the mammal to kill or inactivate autoimmune cells (i.e., cells defective in apoptosis) in the mammal.

Where the mammal is a diabetic human patient, it may be desirable to add a further step of maintaining normal levels of glucose prior to, after, or concurrently with step (b). As described above, maintenance of normal blood glucose levels in a patient with established diabetes may improve the efficacy of the inventive method.

As mentioned previously, re-education of the immune system with MHC class I and peptide can employ cells expressing endogenous peptide in the context of MHC class I or class I /peptide complexes alone. A number of such immune system re-education methods are known, e.g., as described in U.S. Pat. No. 5,538,854, hereby incorporated by reference.

Similarly, a variety of well known methods can be used in the present invention to accomplish ablation of autoimmune cells. One preferred treatment is the administration of TNF-alpha, which is available from Genentech Corporation, South San Francisco, Calif.; Roche; Boehringer Ingelheim; Asahi Chemical Industry; and Sigma Chemicals. The administration intraperitoneally of TNF-alpha to decrease rejection in diabetes-prone mice is described in Rabinovitch et al., *J. Autoimmunity* (1995) 8(3):357–366, hereby incorporated by reference.

Other host treatment methods can be used as well to ablate autoimmune cells, for example, administration of CFA, interleukin-1 (IL-1), proteasome inhibitors, $NF_\kappa B$ inhibitors, anti-inflammatory drugs, tissue plasminogen activator (TPA), lipopolysaccharide, UV light, or an intracellular mediator of the TNF-alpha signaling pathway. Such agents induce the apoptosis of autoreactive lymphocytes by interrupting the pathway downstream from TNF-alpha receptor signaling. Other useful agents are drugs that act downstream of TNF-alpha receptor binding. (Baldwin et al., *Ann. Rev. Immunol.*(1996) 12:141; Baltimore, *Cell* (1996) 87:13).

In other aspects, the invention features a method of increasing the number of functional cells of a predetermined type in an individual diagnosed with an autoimmune disease, by (a) providing a sample of cells of the predetermined type, (b) treating the cells to modify the presentation of an antigen of the cells that is capable of causing an in vivo T-lymphocyte-mediated rejection response, (c) introducing the treated cells into the mammal, and (d) prior to, after, or concurrently with step (c), treating the mammal to kill or inactivate T-lymphocytes of the mammal. This method may be particularly useful for the treatment of advanced-stage autoimmune disease, where complete destruction of a particular cell type or tissue has been achieved.

In preferred embodiments, step (b) involves eliminating, reducing or masking the antigen. A number of methods can be used to modify, eliminate, or mask donor cell antigens; some of these are described in the afore-mentioned Faustman U.S. Pat. No. 5,283,058. For example, step (b) may involve genetically altering the donor animal so that HLA class I or a molecule in its pathway is genetically deleted or chaperone ablated to prevent surface expression. Alternatively, step (b) may involve masking HLA class I antigen using an antibody F (ab')$_2$ fragment that forms a complex with HLA class I.

The therapeutic regimen of the present invention can be used not just to inhibit rejection of regenerating cells, but also to treat autoimmune diseases in which endogenous cell or tissue regeneration is desired, e.g., to allow myelin regeneration (or mere preservation of the remaining autoimmune target cells that are surviving) in multiple sclerosis or joint regeneration in rheumatoid arthritis.

Where the invention is used not just to protect regenerating endogenous cells, e.g., islet cells, from autoimmune attack, but also to protect transplanted cells and tissues, the methods described above can be combined with other, known methods for inhibiting allograft rejection. Such methods include administration of anti-alpha CD3 antibodies, anti-CD40L antibodies (CD40 Ligand, a co-receptor for T cell triggering, to prevent reduction of tolerance in the host), FK506, tacrolimus, sirolimus, alpha-CD25 induction, etc. and cyclosporin A. As is discussed above, autoimmune insulin-dependent diabetes melitus (IDDM) lymphocytes are particularly sensitive to cell death via the TNF-alpha pathway, and thus drugs that potentiate this pathway downstream of receptor binding can be employed. Examples of such potentiating drugs are targets of TRIP, NIK, IκK, TRADD, JUN, NF$_κ$B, Traf2, and proteasome processing etc.

Even when the primary goal is regeneration or rescue of endogenous cells rather than permanent allograft engraftment, it can be useful to implant an allograft and promote its temporary survival, while simultaneously promoting re-education of the immune system so that the endogenous cells can regenerate; autoreactive lymphocytes are detrimental to both the allograft and the regenerating cells, and therefore killing or inactivation of those cells is doubly advantageous.

Thus, in the case of diabetes, for example, transplanted islets can be temporarily protected from rejection by temporary encapsulation or by meticulous blood sugar control with exogenous insulin, while the host is treated, as described above, to kill autoreactive lymphocytes and the immune system is re-educated by methods using class I and peptide or class II and peptide. An additional advantage of using allogeneic islet transplants during this phase is that normal islets that are temporarily protected might provide normal hormonal and secretory capacities which will optimize in situ regeneration and rescue.

Other Embodiments

The skilled artisan will appreciate that the present invention can easily be applied to treat any of a variety of autoimmune disorders. Particularly, the present invention is particularly preferred for the treatment autoimmunity where destruction of a particular cell type or tissue is ongoing. The present invention provides the advantage of providing relief to patients with even established cases of autoimmunity, where tissue destruction is advanced or complete. The present invention will now be demonstrated by the following non-limiting examples.

EXAMPLES

Example 1

Combination Therapy

To devise a clinically applicable protocol for the regeneration of islets in a diabetic host, two therapies were combined and tested in the diabetic NOD mouse (a murine model for human type I diabetes). First, donor B6 islets were protected from graft rejection by temporary class I ablation (class$^{-/-}$) of the β$_2$M gene (Anderson et al., supra; Hyafil et al., supra; Schmidt et al., supra; Bernabeu et al., supra; Li et al., supra). The transgenic donor B6 islets were then removed from the donor mouse and transplanted into the host NOD mouse. Subsequently, a single foot pad injection of CFA was simultaneously administered; a treatment that sustains levels of TNF-alpha for days (Sadelain et al., *Diabetes*, (1990) 39:583–589; McInerey et al., *Diabetes*, (1991) 40:715–725; Lapchak et al., *Clin. Immunol. Immunopathol.* (1992) 65(2):129–134).

The response of severely diabetic NOD female mice to treatments of donor B6 islets with or without transient MHC class I$^{-/-}$ interruption and TNF-alpha induction are summarized in Table 2.

TABLE 2

| | Blood Sugar Control in Diabetic NOD Mice Receiving Islet Transplants | | | |
|---|---|---|---|---|
| Group | Donor | TNF-alpha* Induction | Days of normoglycemia | Mean ± SD |
| #1 | NOD | − | 4, 6, 6, 8, 10 | 9 ± 2.3 |
| #2 | B6 | − | 2, 2, 3, 9, 9, 23 | 8 ± 8.0 |
| #3 | B6-Class I$^{-/-}$ | − | 5, 9, 12, 12, 17, 18, 71 | 22 ± 24 |
| #4 | NOD | + | 30, 55, 61, 70, 72, 121, 136, 137 | 85 ± 40 |

TABLE 2-continued

Blood Sugar Control in Diabetic NOD Mice Receiving Islet Transplants

| Group | Donor | TNF-alpha* Induction | Days of normoglycemia | Mean ± SD |
|---|---|---|---|---|
| #5 | B6 | + | 9, 9, 9, 10, 11 | 10 ± 0.9 |
| #6[†] | B6-Class I$^{-/-}$ | + | 13, 14, 14, 15, 25, 32, 32, 32, 36, >133, >133, >131, >129, >132 | >62 ± 54 |
| #7[††] | B6-Class I$^{-/-,-/-}$ | + | 11, 12, 13, 14, 14, >148 | 35 ± 55 |

*TNF-alpha induction was accomplished with a single foot pad injection of CFA at the time of the transplant.
[†]B6-Class I$^{-/-}$ donor islets represent islets with transient class I interruption due to ablation of the donor $\beta_2$-microglobulin gene ($\beta_2$M).
[††]B6-Class I$^{-/-,-/-}$ donor islets with more permanent class I ablation were isolated from mice with both $\beta_2$M and Tap1 gene interruption, two chaperone proteins essential for class I surface expression.

All hosts were female diabetic NOD mice, typically greater than 20 weeks of age, with sustained blood sugar levels in excess of 400 mg/dl for at least 7 days with the administration of insulin of 0.5 U/kg to prevent death. This dose of insulin typically maintains blood sugar levels of NOD mice diabetic in the normal range of 100–200 mg/dl. Eight to twelve hours prior to transplantation, insulin is stopped. All islet transplants are performed unilaterally under the kidney capsule to facilitate post-transplant islet histology using standard techniques.

Typically, NOD islets isolated form 5–10 week old pre-diabetic female NOD mice are rapidly rejected when transplanted into severely diabetic NOD mice (Table 2, group 1). Similarly, B6 islets transplanted under the kidney capsule of diabetic NOD mice are also rapidly rejected with a mean survival time of 8±8.0 (Table 2, Group 2). As published in the literature, although donor islets with MHC class I$^{-/-}$ ablation survive indefinitely in non-autoimmune hosts (Faustman, 1991, supra), the transient MHC class I ablation only permits a three fold increase in islet survival in the challenging diabetic NOD host. All diabetic NOD hosts eventually reject the B6 class I$^{-/-}$ A donor islets; mean survival is extended to 22±24 days (Table 2, group 3). As shown in Table 2, group 4, although TNF-alpha induction facilitates syngeneic islet transplantation in NOD hosts, this autoimmune directed therapy has minimal effect of B6 islet survival. B6 islets transplanted into diabetic NOD mice with TNF-alpha induction are uniformly rejected by day 10 post-transplantation in all diabetic NOD recipients (Table 2, group 5).

Figure 2:
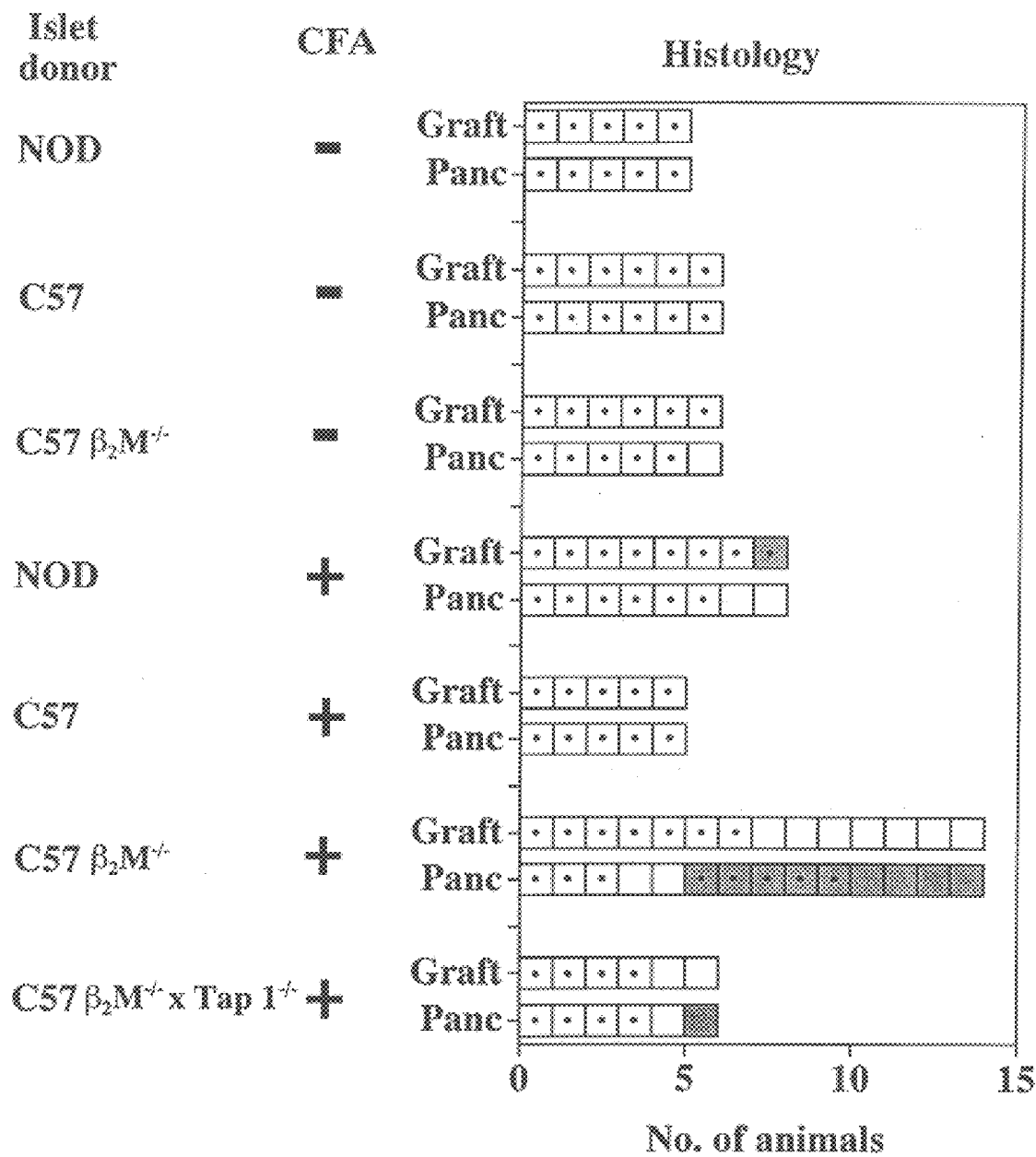
FIG. 2 is a graph depicting the histological characteristics of the graft site and pancreas of individual NOD hosts subjected to transplantation of islets from various types of donors in the absence or presence of TNF-alpha induction. Open squares indicate lack of visible islet structures and of visible lymphocytic accumulation; open squares with dots indicate massive lymphocytic accumulation obscuring islet remnants; shaded squares indicate viable islets without lymphocytes; shaded squares with dots indicate viable islet structures with only circumferential lymphocytic accumulation; panc indicates pancreas.

As shown in FIG. 1, B6 islets isolated from young NOD mice and transplanted into a diabetic NOD mouse with TNF-alpha induction demonstrate severe lymphocytic infiltrates under the kidney capsule at the islet transplantation site (see also, FIG. 2). At the same time, blood sugar levels have increased to what they were prior to transplantation. In addition, the endogenous pancreas shows no intact islets; the remaining isle structures in the pancreas are obscured by dense pockets of infiltrating lymphocytes. Similarly, B6 islets transplanted into an NOD mouse treated with TNF-alpha induction are rejected; the histology is virtually indistinguishable; massive lypocytic infiltrates under the kidney capsule at the transplant site with the endogenous pancreas showing islet structures obliterated with lymphocyte invasion (FIG. 1B).

Importantly, combining MHC class I$^{-/-}$ islet transplantation with TNF-alpha induction in NOD diabetic hosts was successful (Table 2, group 6). Continuous and sustained normoglycemia was observed in 5 of the 14 diabetic NOD hosts; normoglycemia continued beyond 129 days after islet transplantation in the previously diabetic NOD mice receiving the combined treatment. The mean survival time for normoglycemia exceeded 62±54 days. Long-term normoglycemic NOD mice were sacrificed after at least 129 days of post-transplantation monitoring to evaluate the subrenal capsule islet transplantation site and the endogenous pancreas.

Figure 3:
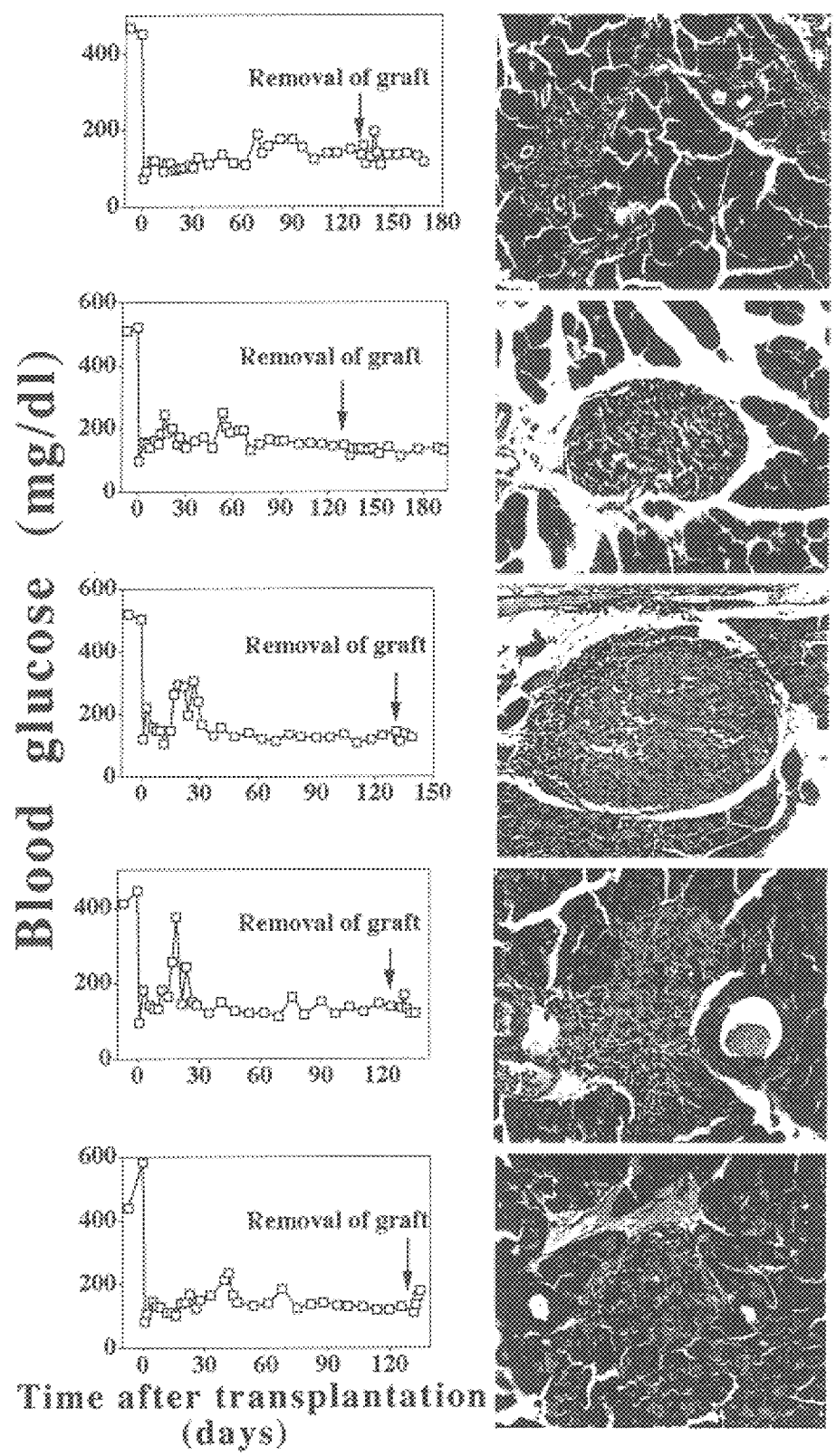
FIG. 3 shows five graphs depicting blood glucose levels (left panels) and five photographs showing the histology of the pancreas (right panels) of diabetic NOD female mice subjected to transplantation with islets from $\beta_2M^{-/-}$ C57 mice and a single injection of CFA. Arrows indicate the time of removal of the kidney containing the islet graft by nephrectomy.

Surprisingly, all 5 long-term normoglycemic NOD mice receiving B6 class I$^{-/-}$ islets with TNF-alpha induction treatment histologically demonstrate no surviving islet grafts under the kidney capsule at 130 days post-transplantation. The endogenous pancreas of these mice demonstrated significant islet regeneration (FIG. 3). Furthermore, the islets in the pancreas lacked lymphocyte invasion or, at most, occasionally demonstrated circumferential lymphocytes surrounding the regenerated islets. As the individual animal histology in Table 3 summarizes, in situ pancreas regeneration was exclusively a trait of diabetic NOD mice treated with TNF-alpha in combination with transplantation of donor islets having transient MHC class I$^{-/-}$ interruption. These results demonstrate that the above combination therapy (administration of TNF-alpha and islet cells temporarily ablated for class I (class I$^{-/-}$)) successfully eliminates existing autoimmunity in severely diabetic NOD mice and promotes regeneration of the endogenous pancreas.

Figure 7:
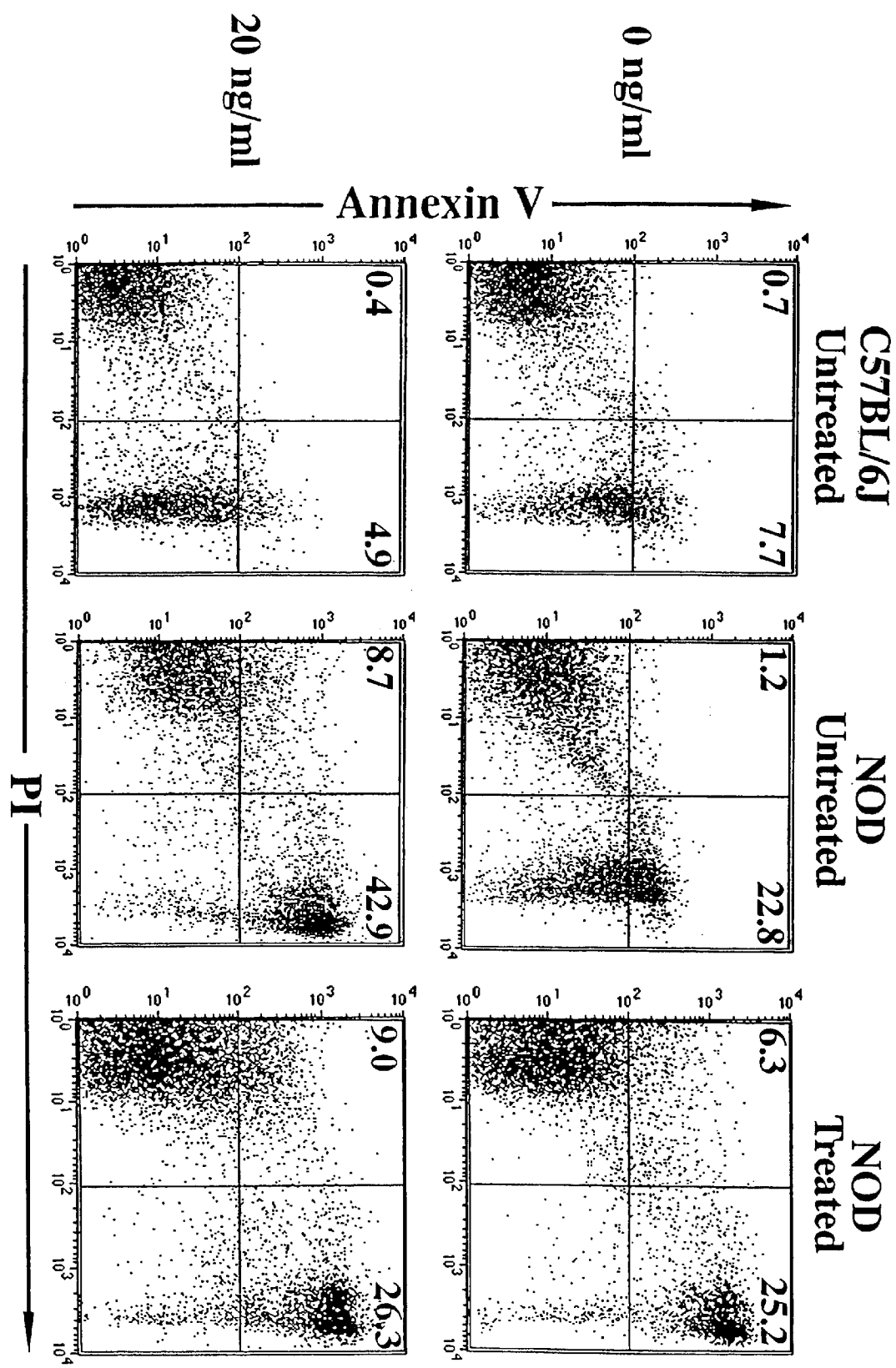
FIG. 7 shows the effects of TNF-alpha on the survival of spleen cells derived from untreated C57 (C57BL/6) and untreated or treated NOD mice. Spleen cells were incubated without or with TNF-alpha (20 ng/ml) for 24 hours after which apoptotic cells were detected by flow cytometry with fluorescein isothiocyanate-conjugated annexin V. The percentage of apoptotic cells is given in the top right-hand corner of each panel.

In addition to the elimination of the existing autoimmunity, elimination of TNF-alpha sensitive cells in NOD mice by combined treatment of CFA and C57 lymphocytes or islets was also observed. As the scientific literature reports, incubation of spleen cells from non-autoimmune C57BL/6 mice treated with TNF-alpha (10–20 ng/ml) had no effect on cell viability. In contrast, high numbers of splenocytes from female NOD mice were killed by apoptosis after 12 hours of low dose TNF-alpha exposure. TNF-alpha induced apoptosis in NOD spleen cells from mice 7–15 weeks of age was confirmed using either trypan blue staining or flow cytometry (FIG. 7). Importantly, splenocytes from formerly diabetic NOD mice which received the therapeutic combined treatment of CFA plus class I positive cells were found to have permanent elimination of TNF-alpha sensitive lymphocyte subpopulations (FIG. 7). In vitro treatment of splenocytes from successfully treated NOD mice with TNF-alpha resulted in little or no cell death beyond that seen in the absence of TNF-alpha.

I have also examined the time course of the appearance and the elimination of TNF-alpha sensitive subpopulations. In pre-diabetic NOD mice, which progress to diabetes, splenocytes were found to have high sensitivity to TNF-alpha induced apoptosis beginning after approximately 7 weeks of age. The timing of the onset of this sensitivity was correlated with a lineage/tissue specific decrease in LMP2 protein. Indeed, splenocytes from LMP2$^{-/-}$ mice have TNF-alpha sensitivity at all ages. Yet, only the combined treatment of CFA and MHC class I donor cells permanently eliminated these TNF-alpha autoreactive cells in autoimmune NOD mice.

Figure 8:
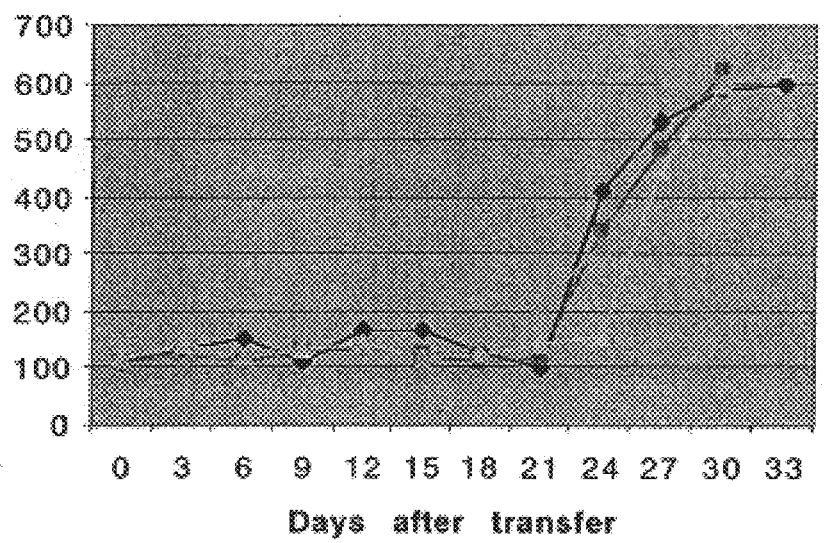
FIG. 8 shows the blood sugar levels in adoptive transfer recipients of fresh untreated spleen cells (top) or in vitro TNF-alpha treated cells (bottom) from diabetic NOD mice transferred to young irradiated male NOD mice. In the top panel, mice were injected with $2 \times 10^7$ spleen cells pooled from three spontaneously diabetic NOD mice. In the bottom panel, recipient mice were also injected with spleen cells pooled from three,spontaneously diabetic NOD mice. Prior to injection, these splenocytes were treated with 10 ng/ml TNF-alpha in vitro and assayed for cell viability. $2 \times 10^7$ viable spleen cells were then injected into recipient mice.
Figure 8:
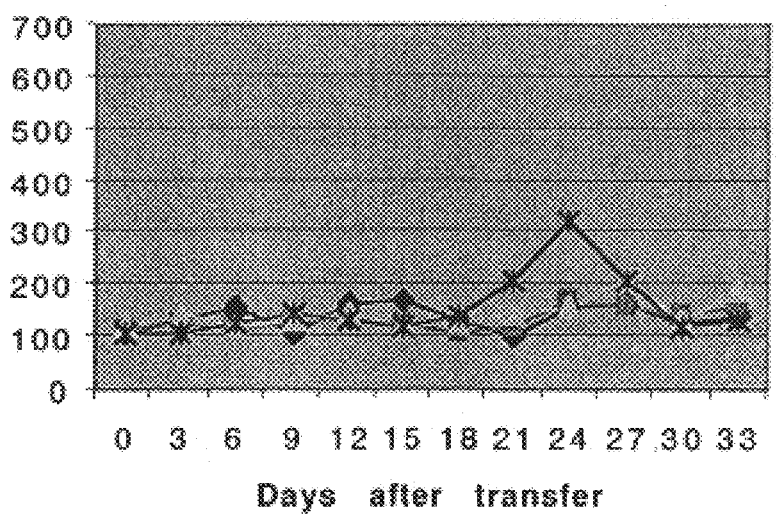

To further prove that the elimination of the TNF-alpha sensitive sub-population of splenocytes is a key feature of the combined treatment of CFA and MHC class I donor cells, I conducted an adoptive transfer experiment. This was accomplished by testing whether diabetes, from spontaneously diabetic NOD mice, can be transferred to healthy irradiated (790R) syngeneic young male NOD mice. In these experiments, I observed that spleen cells from diabetic NOD mice adaptively transferred diabetes into healthy mice, typically within 20–30 days after an injection of $2 \times 10^7$ splenocytes (FIG. 8). Importantly, when the lymphocytes from diabetic mice were treated in vitro with TNF-alpha at 20 ng/ml for 24 hours prior to transfer, diabetes induction was not observed during the 33 days of observation (FIG. 8). Accordingly, treatment of splenocytes with TNF-alpha in vitro has the ability to selectively kill existing disease-causing cells. Although other cell populations may participate in disease expression, their action is not sufficient to enable expression of diabetes in the absence of the TNF-alpha sensitive population.

Furthermore, in these adoptive transfer experiments, all male NOD mice receiving untreated or TNF-alpha treated diabetic lymphocytes, if still normoglycemic, were killed after the onset of diabetes or at day 35. Male NOD mice receiving the untreated diabetic splenocytes became hyperglycemic during the observation period and had their pancreatic islets obliterated by dense infiltrates. All male NOD mice receiving TNF-alpha treated lymphocytes remained normoglycemic, but had mild to moderate invasive insulitis. This indicated that, while diabetes transfer was delayed, diabetes most likely would occur with lengthened observation times. Therefore, TNF-alpha treatment of diabetic splenocytes delays rapid diabetes transfer but does not permanently eliminate T cells with the latent potential to cause disease in the autoimmune prone host.

Indeed, this experimental result is complementary to the pancreatic histology observed in the NOD mice exhibiting diabetes that were treated with CFA alone and shown in FIG. 1. Active autoimmunity defined by invasive insulitis is never eliminated but is reduced in magnitude by CFA treatment alone. To eliminate autoimmunity permanently, other interventions, such as re-introduction of syngeneic MHC class I expressing cells, as described herein, are required.

In addition, NOD diabetic mice successfully treated with the combination of CFA and MHC class I donor cells no longer have TNF-alpha sensitive lymphocyte subpopulations, indicating that this population of disease-causing cells has been eliminated and continues to be permanently eliminated (FIG. 7). Therefore, not only does the brief in vivo therapy with CFA and cells bearing semi-matched MHC class I peptide complexes eliminate existing autoimmune cells but also the combined therapy established permanent elimination of these disease causing cells. Splenocytes from a successfully treated long-term normoglycemic NOD mice do not transfer diabetes after 100 days of observation and the host pancreatic histology revealed no lymphocytic infiltrates.

Example 2

Maintenance of Transplanted Islet Cells is not Required for Regeneration of the Endogenous Pancreas To confirm the ability to eliminate existing autoimmunity and regenerate the endogenous pancreas, additional diabetic NOD mice were transplanted with MHC class I$^{-/-}$ islets under the kidney capsule with TNF-alpha induction. At various times post-transplantation, in the presence of sustained induced normoglycemia, islet grafts placed under the kidney were removed by nephrectomy and survival surgery performed to evaluate whether maintenance of normal blood sugar levels was dependent on presence of the graft. FIG. 3 shows that all five severely diabetic mice that successfully received TNF-alpha induction and B6 MHC class I$^{-/-}$ islet therapy remained normoglycemic at sacrifice times 3 to 60 days after nephrectomy. In addition, the pancreatic histology in all five hosts revealed a surprising number of pancreatic islets, with minor numbers of circumferential lymphocytes or no lymphocytes surrounding the regenerated and rescued islets. Evaluation of all islet transplant sites under the kidney demonstrated no surviving transplanted islets.

In marked contrast, all NOD mice receiving syngeneic NOD islet cells by transplantation, in conjunction with TNF-alpha induction, rapidly returned to hyperglycemia post-transplantation, demonstrating failure of this transplant protocol using syngeneic NOD islets to promote endogenous pancreatic islet cell regeneration.

Example 3

Temporary Class I$^{-/-}$ Ablation is Critical for Successful Combination Therapy Treatment In order to begin to dissect the mechanism of systemic reestablishment of tolerance sufficient for pancreatic islet re-growth, additional experiments were performed. In order to achieve a higher success rate of pancreatic islet regeneration with eliminated autoimmunity, a more permanent MHC class I ablated islet was tested in the combination therapy treatment. Islets from B6 donors with both ablated $\beta_2$M and Tap 1 genes (MHC class I$^{-/-,-/-}$), the obligatory chaperone and transport proteins for MHC assembly, respectively, were transplanted into severely diabetic NOD mice with TNF-alpha induction. I found that although this approach is effective at prolonging normoglycemia in murine hosts without autoimmunity, this treatment failed to prolong normoglycemia in the autoimmune, diabetic NOD host. More permanent donor MHC class I elimination with TNF-alpha induction in the diabetic NOD host culminated in rapid islet graft rejection and poor ability to achieve endogenous islet regeneration (Table 2, group 7). Apparently, some expression of donor MHC class I and self peptide is essential for NOD tolerance induction to self antigens, even if only for a limited time, on average 20 days (Table 2, group 3) before transplant rejection.

Example 4

Injection of Temporarily Ablated Islet Cells is Sufficient for Induction of Endogenous Pancreas Regeneration Based on the data of Example 3, above, I proposed that class I+ lymphocyte immunizations could be an efficacious therapy, even if the donor cells only survived a short time in vivo post-injection. In order to test this theory, nine diabetic NOD mice with severe hyperglycemia were initiated on a 40 day regimen of one bolus injection of CFA to transiently induce TNF-alpha and biweekly exposures by intravenous (IV) injection of B6 splenocytes ($9 \times 10^6$ splenocytes IV). B6 splenocytes are a lymphoid cell population with intact MHC class I and self peptide presentation that survives only transiently in vivo due to rejection by the host.

Additionally, four diabetic control NOD mice were maintained over the same time period with only insulin treatment. All control NOD mice were monitored every other day for hyperglycemia and insulin was administered daily unless normoglycemia returned. After approximately 40 days of treatment, all control NOD mice receiving only insulin were dead. Poor blood sugar level control, cachexia, and weight loss accounted for the uniform mortality of all diabetic NOD hosts by day 20 (FIG. 4A). Control mice treated only with insulin also had pancreatic histology demonstrating impressive lymphoid infiltrates obscuring any recognizable islet structure (FIG. 4C).

Figure 4:
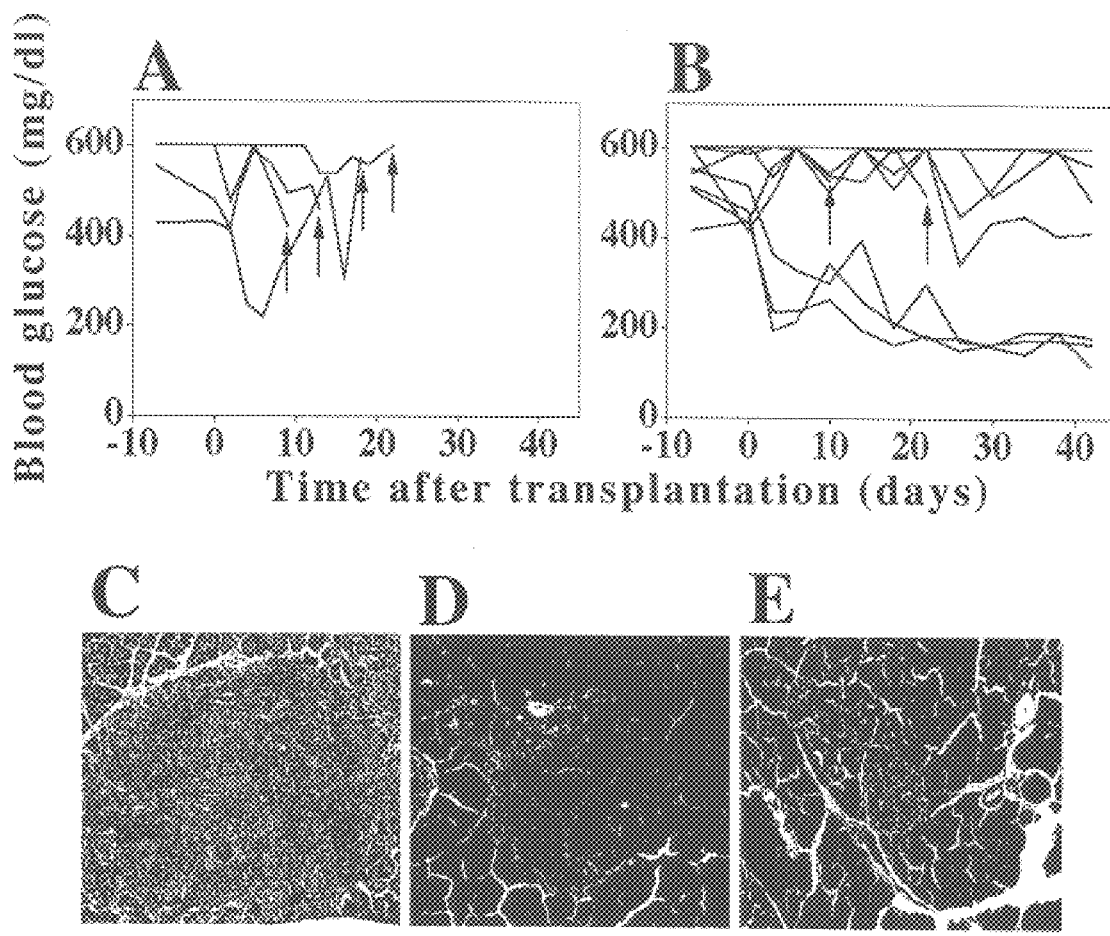
FIG. 4 shows two graphs (panels A and B) and three photographs (panels C, D, and E) that demonstrate the effect of TNF-alpha induction and repeated exposure to C57 splenocytes on islet regeneration and restoration of normoglycemia in diabetic NOD hosts. Panel A represents NOD females treated with daily injections of insulin alone (controls, n=5). Panel B represents NOD females treated with insulin (until normoglycemia was restored) plus a single injection of CFA and biweekly injections of $9 \times 10^6$ C57 splenocytes (n=9). Arrows represent time of death. Pancreatic histology of a control animal (panel C); an animal that remained hyperglycemic (panel D); and an animal in which normoglycemia was restored (panel E).

In marked contrast, nine severely diabetic NOD mice receiving repeat exposures to B6 splenocytes plus TNF-alpha induction were alive in eight of nine cases and three of the NOD mice had returned to normoglycemia by day 40. In addition, four diabetic NOD mice treated with repeat B6 splenocyte immunization and TNF-alpha induction, had improved islet histology by day 40 (FIG. 4D). Pancreatic islets were visible and lymphoid infiltrates were significantly reduced circumferentially as well as adjacently to the islet structures. This pattern is characteristic of a histology pattern of protective, not destructive, lymphocyte infiltrates (Gazda et al., *Journal of Autoimmunity* (1997) 10(3) :261–70; Dilts et al., *Journal of Autoimmunity* (1999) 12(4) :229–32). Three diabetic NOD mice with TNF-alpha induction and B6 splenocyte immunizations produced complete islet regeneration and insulin independence. Histology on these three mice revealed dramatically reduced lymphocytic autoreactivity and increased islet abundance (FIG. 4D). Therefore, combined treatment with TNF-alpha induction and repeated exposure to peptide-bound B6 MHC class I lymphocytes was sufficient to transiently obliterate autoreactive T cells and reverse NOD diabetes for at least 40 days in approximately 30% of the hosts tested (FIG. 4). The therapy was partially protective in approximately 50% of the NOD hosts (FIG. 4).

In order to eliminate poorly controlled blood sugar levels as a factor hampering more complete islet regeneration, additional groups of diabetic NOD mice were similarly treated, with TNF-alpha induction and B6 splenocyte injection, but with simultaneous implantation of a euglycemic clamp intraperitoneally, for 40 days. A murine euglycemic clamp in these studies consisted of alginate encapsulated B6 islets. The alginate capsule provides a membrane barrier system that allows short term glycemic control of insulin exchange but prevents direct cell-cell contact (e.g., for T cell education). After 40 days, the euglycemic NOD mice with the encapsulated islets underwent surgical removal of the alginate capsules and the blood sugar levels of the diabetic NOD mice were monitored for evidence of in situ pancreas regeneration.

Table 3, shows that after 40 days, both mice treated with the euglycemic clamp in the absence of TNF-alpha induction (Table 3, group 1) and mice treated with the euglycemic clamp and TNF-alpha induction (Table 3, group 2), showed an absence of endogenous islet regeneration and rapidly returned to hyperglycemia after clamp removal. Results indicate that under conditions of excellent glucose control and TNF-alpha induction, apoptosis of existing autoreactive cells is induced during the early phases of acute diabetes, but neither the degenerative state of the pancreas (as assayed by histology) nor the course of preexisting autoimmunity can be altered. The histology of NOD control treatment groups consisted of severe lymphocytic elimination of the islets in the pancreas (Table 3, FIG. 4).

TABLE 3

Impact of short-term (40 day) blood sugar control on endogenous islet regeneration in diabetic NOD mice after removal of euglycemic clamp

| Group | Spleen cell donor | TNF-alpha induction* | # of normoglycemic recipients Total # of recipients | % |
|---|---|---|---|---|
| 1 | — | − | 0/7 | 0 |
| 2 | — | + | 0/6 | 0 |
| 3 | B6 | + | 7/9 | 78 |
| 4 | B6 class I$^{-/-,-/-}$ | + | 2/6 | 33 |
| 5 | C57 class II$^{-/-,+/+}$ | + | 8/11 | 73 |

*Euglycemia was maintained for 40 days with an encapsulated islet allograft that was surgically removed on day 40. All the encapsulated grafts were removed on day 40 after transplantation.
¶Another five recipients rejected the encapsulated grafts before removal of the grafts precluding the determination of euglycemia in islet regeneration.
††C57-class II$^{-/-}$ cells were from disruption of the Abb gene and expresses no A or E MHC class II molecules and were purchased from Taconic Research Laboratories (Germantown, NY).
*TNF-alpha induction was accomplished with a single foot pad injection of CFA at the time of the first spleen cell injection of 9 × 10$^6$ cells IV.
†B6 class I$^{-/-,-/-}$ donor splenocytes were from mice with both β$_2$M and Tap1 gene interruption.

In marked contrast, diabetic NOD mice that had received biweekly B6 splenocyte immunizations in combination with a single dose of TNF-alpha induction therapy remained normoglycemic for 40 days after clamp removal in 78% of the cases. A total of nine diabetic NOD mice were treated with this therapy and seven of the nine NOD mice had pancreatic histology that demonstrated sustained and continuing islet regeneration days to weeks after euglycemic clamp removal (Table 3, FIG. 5). In general, host islets had circumferential lymphocytic accumulations and in some cases were aldehyde fuschin positive, (i.e., had excess insulin, beyond the amount to maintain normoglycemia).

Therefore, islet regeneration was optimized in established diabetic NOD mice by maintenance of blood glucose levels (using a euglycemic clamp), ablation of autoreactive lymphocytes (by brief TNF-alpha induction), and repeated exposure to MHC class I and peptide presenting cells, after a 40 day course of bi-weekly B6 splenocyte injections. Furthermore, after the therapy was halted and autoimmunity eliminated, the immediate rescue and continuous expansion of the endogenous pancreas was sufficient for sustained tolerance to self antigens. The mechanism of splenocyte re-education was defined as dependent upon the education complex of MHC class I and endogenous peptides. As demonstrated in Table 3, injection of splenocytes permanently ablated for MHC class I proteins (MHC class I$^{-/-,-/-}$) into diabetic NOD mice with euglycemic clamps led to poor in situ islet regeneration (Table 3, group 4, FIG. 5). Injection of splenocytes lacking MHC class II proteins (MHC class II$^{-/-}$) permitted in situ islet regeneration presumably due to continued expression of endogenous peptide in the context of MHC class I (Table 3, group 5, FIG. 5). Reestablishment of self tolerance and elimination of autoreactivity was MHC class I dependent and MHC class II independent. The sustained effectiveness of this treatment is demonstrated in FIG. 5. Blood sugar maintenance was observed beyond 20 days after the removal of the euglycemic clamp.

Example 5

Regeneration of the Endogenous Pancreas

Generally, the percentage of CD3$^+$ T cells in young NOD mice (<12 weeks of age) is low, but after 30 weeks of age the percentage of CD3$^+$ T cells increases dramatically and exceeds that of control mice. In order to evaluate the impact of successful pancreas regeneration and rescue on NOD lymphocyte selection, flow cytometric analysis was performed on CD3$^+$ T cells from treated NOD mice.

Figure 6:
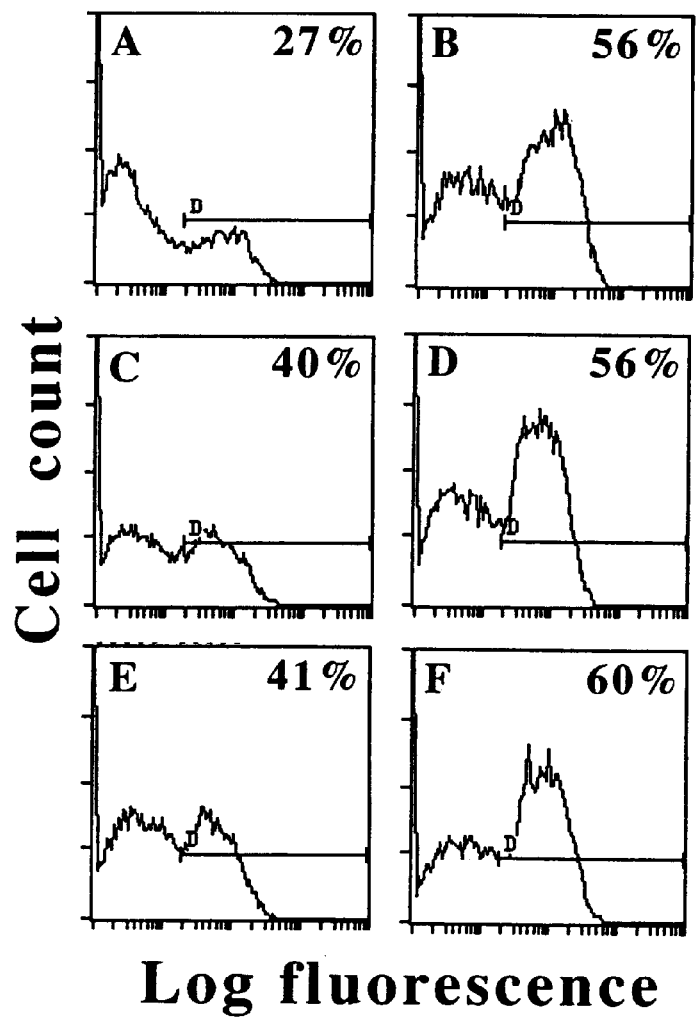
FIG. 6 shows six graphs depicting flow cytometric analysis of the effect of islet regeneration on the percentage of CD3$^+$ T cells among splenocytes of NOD mice. Percentage CD3$^+$ cells is shown in the upper right corner of each graph. Panel A represents a 6- to 7-month-old female C57 mouse; panel B represents a diabetic NOD female treated with insulin alone for 12 days; panels C through F represent diabetic NOD females implanted with a euglycemic clamp for ~40 days and treated with a single injection of CFA either alone (panel D) or together with biweekly injections of normal C57 splenocytes (panel C), MHC class II$^{-/-}$ C57 splenocytes (panel E), or $\beta_2M^{-/-}$, TAP1$^{-/-}$ C57 splenocytes (panel F).

Splenic CD3$^+$ T cell percentages were evaluated in 5 treated NOD mice receiving various treatments; represented in FIG. 6 at 5 to 26 days after treatment had stopped. An untreated age-matched NOD female mouse treated with insulin had 56% of splenocytes staining with anti-CD3 antibodies. The age-matched B6 female mouse had 27% positive splenocytes (FIG. 6), a trend previously reported (Miyazaki Clin. Exp. Immunol. 85:60,622; Pontesilli Clin. Exp. Immunol. 97:70,84). Two mice were successfully treated through either B6 or B6 class II$^{-/-}$ splenocyte immunizations, in conjunction with TNF-alpha induction, and displayed pancreas rescue and regeneration. Remarkably, both successfully treated NOD mice had 40% of splenocytes staining with anti-CD3$^+$ antibodies (FIG. 6). In marked contrast, unsuccessfully treated age matched NOD mice (treated with only TNF-alpha induction therapy or TNF-alpha induction therapy in conjunction with B6-MHC class I$^{-/-}$ splenocytes) had no alterations in the high number of splenic CD3$^+$ cells (FIG. 6). Therefore, the impact of halted autoimmunity and re-establishment of tolerance was systemic and included markedly altered T cell selection that partially normalized numbers of CD3$^+$ T lymphocytes in the spleen. These observations were further affirmed by my results which showed that (1) successful therapy results in a substantial reduction in naive T cells expressing CD45RB$^{high}$, CD62L, and CD95 proteins and (2) an increase in the number of long-term memory cells, both indications of the normalization of T cell selection as a result of the combination therapy.

Example 6

Identification and Elimination of Autoimmune Cells

TNF-alpha sensitivity, in the NOD mouse, results from signaling defects in the NF$_\kappa$B/proteasome activation pathway, thereby permitting the TNF-alpha combination treatment disclosed herein to be successful. Accordingly, the methods disclosed herein are applicable to any number of mammalian systems. For example, I have shown that TNF-alpha induced apoptosis also occurs in humans. In my studies using fresh human lymphocytes, from patients with diverse autoimmune diseases, use of the combination of CFA and MHC class I donor cells resulted in TNF-alpha induced apoptosis of autoreactive lymphocytes. Lymphocytes from patients with type I diabetes (n=80), multiple sclerosis (n=5), and rheumatoid arthritis (n=10), were treated in vitro with 10–20 ng/ml of TNF-alpha for 24 hours and then evaluated for cell viability. Control lymphocytes from normal human donors were also studied (n=80). In all cases, the control cells were found to be protected from cell death. In contrast, all lymphocytes from autoimmune samples showed varying degrees of cell death after TNF-alpha exposure. These results support the above-described notion that humans with diverse autoimmune diseases, similar to the NOD mice, have intracellular defects in signaling pathways such as NF$_\kappa$B, preventing normal viability after exposure to this cytokine, TNF-alpha. Additional data from this study of humans has revealed that the severity of the autoimmune cell death after TNF-alpha treatment relates to the rate of onset of the disease not to the duration of the disease. This means, for example, that early onset of diabetic autoimmunity in a four-year old child is associated with a greater fraction of lymphocytes dying after TNF-alpha treatment than is observed, following the same treatment, in lymphocytes from a twenty-year old person with onset of autoimmunity in early adulthood. Accordingly, it is likely that more aggressive autoimmune diseases, e.g., ones that appear earlier during a patient's lifetime, show a greater fraction of autoimmune cells susceptible to the treatment for autoimmune disease reversal as is discussed herein.

Example 7

Treatment of Sjorgen's Disease, RA, and Lupus

As detailed above, the therapeutic methods disclosed herein are readily applicable to any number of autoimmune diseases. For example, when a TNF-alpha treatment regimen combined with exposure to MHC class I-self peptide complexes was applied to other forms of autoimmune disease, such as murine models of Sjogren's disease, lupus symptomatology, and rheumatoid arthritis, I determined that autoimmune infiltrates indicative of Sjogren's disease were eliminated in the salivary and lachrymal glands, autoantibodies indicative of lupus were eliminated, and in a model of rheumatoid arthritis (RA), treatment of female RA mice with the therapy of this application halted limb swelling. The endpoint of a therapy effectiveness was monitored by gross inspection, histology of the target organ, and serology. With respect to RA, after disease onset, nearly 90% of the mice with severe RA were successfully treated and the accompanying joint disease was no longer detectable by gross inspection or by histologic evidence at the time of death.

Example 8

In Vitro Monitoring
Treatment Scenario II

Prescreening: A human subject presenting symptoms of type I diabetes will be brought into the clinic to give a single blood donation that will be divided into two tubes. One tube will be used to screen for the presence of autoantibodies and the other tube will be used in an in vitro screen for apoptotic cell death (e.g., TNF-induced) or accelerated cell death due to any environmental or chemical agent. This initial sample will be used to obtain a base line C-peptide level and to verify the absence of functional islets. Heightened in vitro sensitivity to cell death by any apoptotic cell death pathway will be a prerequisite to future therapy.

Treatment of Juvenile Onset Diabetes: If autoantibodies to islet cells are present, we will conclude that the pancreas is still attempting to regenerate. Thus, if existing autoimmunity was eliminated by treatment, the islets could successfully regrow.

An inexpensive approach to try to immediately rescue the pancreas would be to repeatedly perform BCG administrations, as a non-specific immunostimulant that could successfully raise the levels of endogenous TNF-alpha activity. Endogenous TNF-alpha will kill only the autoimmune cells (i.e., cells with a defect in protection from apoptosis). Initially we will start out with weekly BCG immunization. Blood samples will be collected within 24–48 hours after BCG immunization and tested in vitro (in cell culture) for the persistence of TNF-alpha sensitive autoimmune cells. The isolated cells, grown in cell culture, will be examined to determine whether the autoimmune cells, sensitive to death, are eliminated or reduced by this administration.

If the response to BCG immunization is positive, we will then start immunization with donor lymphocytes. Ideally, these lymphocyte immunizations could be from both parents and would involve weekly infusions into the diabetic child, to be administered simultaneously with the BCG immunizations. In some cases, the donor lymphocytes will be irradiated to decrease the risk of infection transfer. We will introduce the lymphocytes intravenously at a dose of approximately $9 \times 10^6$ to $9 \times 10^9$ as a start. With the in vitro monitoring assay, we expect to be able to identify an optimal dose. Our goal is to continue this treatment from a minimum of 40 days up to about 6 months, or until positive human C peptide is found in the blood and insulin dosing is reduced. Early signs of possible tolerance induction success might not only be the presence of C peptide but also the absence of TNF-alpha sensitive (autoreactive) cells. This would be an indication that the re-education is complete. Also, we predict that the phenotype of peripheral lymphoid cells would possibly convert to a more mature phenotype (shown by an decreased CD45RA to CD45RO ratio). Thus, screening in the lab will involve cell death assays and lymphocyte surface markers of improved T cell selection. We expect also to see gross changes, such as reselection of peripheral T cells and gross numbers of CD3 cells decreasing due to reintroduction of lymphoid cells directly, or due to regeneration of islets that re-select peripheral T cells.

Treatment of Adult Onset Diabetes: If the patient is 40 years old and has had diabetes for 20 or more years, we will follow the same treatment protocol, but extend treatment over a longer period of time. In long standing disease, it is possible that the islet precursor cells of the pancreas are effectively inactive and can no longer multiply because of years of autoimmune attack. This treatment might protect the patient from complications of the disease, which in some cases may be directly related to the altered cytokines of the poorly selected lymphoid cells causing fibrosis. In addition, this treatment might eliminate the autoreactive cells that cause fibrosis and other complications. Lastly, this treatment might allow, for the first time, for islets to be transplanted with the barrier being only islet survival, not islet survival from graft rejection or islet survival against autoimmunity.

Treatment Scenario II

Subjects. Patients who are older than age 18 but younger than 45 years and who have Type 1 diabetes (insulin dependent and ketosis prone) will be recruited for this study. Participants will have to have a duration of Type 1 diabetes, dated from the time of insulin administration, of at least one month, but not more than 5 years. The rationale for the duration criterion is predicated on the expectation that persons with less than 5 years duration will still have residual beta cell mass which is capable of recovery. Patients will be screened to determine whether they have autoantibodies (anti-GAD and anti-IA-2 or islet cell antibodies) present. In addition, the presence of functioning beta-cell mass, as measured by detectable (>0.2 pmol/ml) C-peptide levels after glucagon stimulation, will be determined, although it will not be a requirement for inclusion in the study. Exclusion criteria will include persons who have had previous BCG vaccination, a history of clinical tuberculosis, or positive PPD test, a positive response to an intermediate (5 IU) PPD test, or any acute or chronic skin conditions.

Study Procedures: Eligible volunteers, as judged by chart review, will be asked to come to the Diabetes Research Center where they will have measured both fasting and stimulated (6 min after 1 mg glucagon given IV) C-peptide (endogenous insulin) secretion. In addition, blood samples will be obtained to measure autoantibody status (see above) and the level of TNF and autoreactive T-lymphocytes or peripheral lymphoid cells with apoptosis sensitivity. Finally, if no recent (within four weeks) hemoglobin A1c level is available, one will be obtained. A standard panel of liver function tests and a CBC with differential will also be obtained.

TNF-alpha induction, for example, by CFA administration or BCG "vaccination," will be performed with a standard method with a percutaneous injection of 0.3 ml of a 50 mg/ml solution (Organon)(equivalent to a TNF-alpha induction of 10 $\mu g/m^2$) into the deltoid area. After the BCG solution is topically applied to the skin, a sterile multipuncture disc is used to administer to BCG percutaneously.

Volunteers will be asked to return at weekly intervals for four weeks to have a blood specimen obtained to repeat measurements of TNF and auto-reactive lymphocytes (1 green top and 1 red top tube). The vaccination site (deltoid area) will be examined on each of these occasions to determine whether any significant ulceration or local reaction has occurred. In addition, patients will be questioned with regard to any febrile or other systemic symptoms that may have occurred. After four weeks, the patients will have a repeat vaccination performed in the opposite arm and similar, weekly monitoring will go on for another two months.

Depending on the results from the first group of 5 subjects, adjustments in dosage and/or frequency of BCG vaccination will be made for a subsequent group of 5 individuals.

Risks: The risks entailed in this study are minor and include the minor discomfort of obtaining blood samples. The total volume of blood obtained over the course of the three-month study will be considerably less than usually given in a single blood donation. The glucagon stimulated C-peptide test is commonly used in experimental protocols. The glucagon injection may be associated with mild nausea which usually dissipates in 5 minutes. Rarely (less than 1 in 20) subjects may vomit after glucagon.

BCG vaccination have been used for more than 30 years in many countries, including Canada and in western Europe, as a vaccination against tuberculosis. The recognized side effects of BCG vaccination include mild local discomfort at the vaccination site with a papular rash developing at the site 10–14 days after vaccination and reaching a maximal diameter of 3 mm 4–6 weeks after vaccination. The rash may scale thereafter, and rarely leaves a visible scar. Local adenopathy is rarely seen in children, but almost never in adults. Rare events include osteomyelitis, lupoid reactions, disseminated BCG infections and death. The frequency of these severe reactions is between 1 in 1,000,000 and 1 in 5,000,000 vaccinations, and have occurred almost exclusively in immunosuppressed children. Most of the recent experience with BCG has been in the intravesicular treatment of bladder cancer, where weekly installations of BCG are performed for $\geq 6$ weeks. Finally, BCG vaccination has been used in Type 1 diabetes without any adverse consequences noted.

All references cited herein are hereby incorporated by reference in their entirety.

What is claimed is:

1. A method of increasing or maintaining the number of functional cells of a predetermined type in a mammal, said method comprising the steps of:
   a) providing a sample of cells of said predetermined type,
   b) treating said cells to modify the presentation of an antigen of said cells that is capable of causing an in vivo autoimmune cell-mediated rejection response,
   c) introducing said treated cells into said mammal, and
   d) prior to, after, or concurrently with step c), treating said mammal to kill or inactivate autoimmune cells of said mammal.

2. The method of claim 1, wherein said mammal is a human patient.

3. The method of claim 2, wherein said cells are insulin-producing islet cells.

4. The method of claim 1, wherein step b) comprises eliminating, reducing, or masking said antigen.

5. The method of claim 1, wherein step d) comprises administering to said mammal TNF-alpha or a TNF-alpha inducing substance.

6. The method of claim 5, wherein the TNF-alpha inducing substance is tissue plasminogen activator, LPS, interleukin-1, UV light, or an intracellular mediator of the TNF-alpha signaling pathway.

7. The method of claim 1, wherein said mammal has a mutation in the lmp2 gene or equivalent thereof.

8. A method of increasing the number of functional cells of a predetermined type in a mammal, said method comprising the steps of:
   a) treating said mammal with an agent that kills or inactivates autoimmune cells of said mammal;
   b) periodically monitoring the cell death rate of said autoimmune cells; and
   c) periodically adjusting the dosage of said agent administered to said mammal based on the monitoring of step b).

9. The method of claim 8, wherein said agent comprises TNF-alpha, a THF-alpha inducing substance, tissue plasminogen activator, LPS, interleukin-1, UV light, or an intracellular mediator of the TNF-alpha signaling pathway.

10. The method of claim 5, wherein step d) comprises administering to said mammal two agents that increase TNF-alpha.

11. The method of claim 8, wherein step a) comprises administering to said mammal two agents that increase TNF-alpha.

12. A method for diagnosing an autoimmune disease or the predisposition to said disease in a mammal, said method comprising the steps of:
   a) providing peripheral cells from a mammal,
   b) treating said cells with a TNF-alpha treatment regimen, and
   c) detecting cell death of said peripheral cells, wherein an increase in cell death, when compared with control cells, is indicative of said mammal having an autoimmune disease or a predisposition to said disease.

13. The method of claim 12, wherein said peripheral cells comprise splenocytes, T lymphocytes, B lymphocytes, or cells of bone marrow origin.

14. The method of claim 12, wherein said mammal is a human patient.

15. The method of claim 12, wherein said TNF-alpha treatment regimen comprises treating said peripheral cell with TNF-alpha.

* * * * *